US009005955B2

(12) United States Patent
Goodenough et al.

(10) Patent No.: US 9,005,955 B2
(45) Date of Patent: Apr. 14, 2015

(54) BUOYANT TRIACYLGLYCEROL-FILLED GREEN ALGAE AND METHODS THEREFOR

(71) Applicant: Washington University, St. Louis, MO (US)

(72) Inventors: Ursula Goodenough, St. Louis, MO (US); Carrie Goodson, St. Louis, MO (US)

(73) Assignee: Washington University, Saint Louis, MO (US)

( * ) Notice: Subject to any disclaimer, the term of this patent is extended or adjusted under 35 U.S.C. 154(b) by 0 days.

(21) Appl. No.: 13/662,549

(22) Filed: Oct. 29, 2012

(65) Prior Publication Data

US 2013/0203133 A1 Aug. 8, 2013

Related U.S. Application Data

(60) Provisional application No. 61/552,435, filed on Oct. 27, 2011.

(51) Int. Cl.
| | |
|---|---|
| *C12N 1/12* | (2006.01) |
| *C12N 15/74* | (2006.01) |
| *C12N 9/12* | (2006.01) |
| *C12P 7/64* | (2006.01) |

(52) U.S. Cl.
CPC ........ *C12N 15/74* (2013.01); *C12N 1/12* (2013.01); *C12N 9/1241* (2013.01); *C12Y 207/07027* (2013.01); *C12P 7/6463* (2013.01)

(58) Field of Classification Search
None
See application file for complete search history.

(56) References Cited

U.S. PATENT DOCUMENTS

2014/0030771 A1* 1/2014 Yu et al. .............. 435/134

OTHER PUBLICATIONS

Shin et al., Can. J. Bot, vol. 79: 1083-1089 (2001).*
Franklin et al., Current Opinion in Plant Biology 2004, vol. 7: 159-165.*
*Chlamydomonas* Resource Center, retrieved from the internet: http://chlamycollection.org/strain/cc-4348-sta6-1-mt-ball-bafj5/.*
Docampo, R., Ulrich, P., Moreno, S.N.J. (2010). Evolution of acidocalcisomes and their role in polyphosphate storage and osmoregulation in eukaryotic microbes. Phil. Trans. R. Soc. B 365: 775-784.
Fan, J., Andre, C., and Xu, C. (2011). A chloroplast pathway for the de novo biosynthesis of triacylglycerol in *Chlamydomonas reinhardtii*. Febs Letts. 585: 1985-1991.
Gorman, D.S., and Levine, R.P. (1965). Cytochrome f and plastocyanin: their sequence in the photosynthetic electron transport chain of *Chlamydomonas*. Proc. Natl. Acad. Sci. USA 54: 1665-1669.
Halim, R., Gladman, B., Danquah, M.K., and Webley, P.A. (2011) Oil extraction from microalgae for biodiesel production. Bioresource Tech. 102: 178-85.
Zabawinski, C., Van Den Koornhuyse, N., D'Hulst, C., Schlichting, R., Giersch, C., Delrue, B., Lacroix, J.M., Preiss, J., and Ball, S. (2001). Starchless mutants of *Chlamydomonas reinhardtii* lack the small subunit of a heterotetrameric ADP-glucose pyrophosphorylase. J. Bacteriol. 183: 1069-1077.
Kropat, J., Hong-Hermesdorf, A., Casero, D., Ent, P., Castruita, M., Pellegrini, M., Merchant, S.S., and Malasarn, D. (2011). A revised mineral nutrient supplement increases biomass and growth rate in *Chlamydomonas reinhardtii*. Plant J. 66: 770-780.
Li, Y., Han, D., Hu, G., Dauvillee, D., Sommerfeld, M., Ball, S., and Hu, Q. (2010a). *Chlamydomonas* starchless mutant defective in ADP-glucose pyrophosphorylase hyper-accumulates triacylglycerol. Metab. Eng. 12: 387-391.
Li, Y. Ham, D. Hu, G. Sommerfeld, M., and Hu, Q. (2010b). Inhibition of starch synthesis results in overproduction of lipids in *Chlamydomonas reinhardtii*. Biotechnol. Bioeng. 107: 258-268.
Martin, N.C. And Goodenough, U.W. (1975). Gametic differentiation in *Chlamydomonas reinhardi*. I. Production of gametes and their fine structure. J. Cell Biol. 67: 587-605.
Miller, R., Wu, G., Deshpande, R.R., Vieler, A., Gartner, K., Li, X., Moellering, E.R., Zauner, S., Cornish, A.J., Liu, B. Bullard, B., Sears, B.B., Kuo, M-H., Hegg, E.L., Shachar-Hill, Y., Shiu, S-H., and Benning, C. (2010). Changes in transcript abundance in *Chalmydomonas reinhardtii* following nitrogen deprivation predict diversion of metabolism. Plant Physiol. 154: 1737-1752.
Moellering, Er., and Benning, C. (2010). RNA interference silencing of a major lipid droplet protein affecting lipid droplet size in *Chlamydomonas reinhardtii*. Eukaryot. Cell 10: 97-106.
Ruiz, F.A., Marchesini N., Seufferheld, M., Govindjee, and Docampo, R. (2001). The polyphosphate bodies of *Chlamydoonas reinhardtii* possess a proton-pumping pyrophosphatase and are similar to acidocalcisomes. J. Biol. Chem. 276: 46196-46203.
Schmidt, M.A., and Herman, E.M. (2008). Suppression of soybean oleosin produces micro-oil bodies that aggregate into oil body/ER complexes. Mol. Plant 1: 910-924.
Siaut, M., Cuiné. S., Cagnon, C., Fessler, B., Nguyen, M., Carrier, P., Beyly, A., Beisson, F., Triantaphylidès, C., Li-.Beisson, Y., and Peltier, G. (2011). Oil accumulation in the model green alga *Chlamydomonas reinhardtii*: characterization, variability between common laboratory strains and relationship with starch reserves. BMC Biotechnology 11: 7-22.

(Continued)

*Primary Examiner* — Allison Fox
*Assistant Examiner* — Yvonne Pyla
(74) *Attorney, Agent, or Firm* — Saul L. Zackson; Zackson Law LLC

(57) ABSTRACT

Cultures of *Chlamydomonas* are disclosed comprising greater than 340 mg/l triacylglycerols (TAG). The cultures can include buoyant *Chlamydomonas*. Methods of forming the cultures are also disclosed. In some embodiments, these methods comprise providing *Chlamydomonas* growing in log phase in a first culture medium comprising a nitrogen source and acetate, replacing the first culture medium with a second medium comprising acetate but no nitrogen source, and subsequently supplementing the second medium with additional acetate. In some embodiments, a culture can comprise at least 1,300 mg/l triacyglycerols. In some embodiments, cultures can be used to produce a biofuel such as biodiesel.

21 Claims, 19 Drawing Sheets

(56) References Cited

OTHER PUBLICATIONS

Wang, Z.T., Ullrich, N., Joo, S., Waffenschmidt, S., and Goodenough, U. (2009). Algal lipid bodies: Stress induction, purification, and biochemical characterization in wild-type and starchless *Chlamydomonas reinhardtii*. Eukaryot. Cell 1856-1868, vol. 8, No. 12.

Weers, P.M., and Gulati, R.D. (1997), Growth and reproduction of *Daphnia galeata* in response to changes in fatty acids, phosphorus, and nitrogen in *Chlamydomonas reinhardtii* Limnol. Oceanogr. 42:1584-9.

Work, V.H., Radakovitz, R., Kinkerson, R.E., Meuser, J.E., Elliot, L.G., Vinyard, D.J., Laurens, L.M.L., Dismukes, G.C., and Posewitz, M. C. (2010). Increased lipid accumulation in the *Chlamydomonas reinhardtii* sta7-10 starchless isoamylase mutant and increased carbohydrate synthesis in complemented strains. Eukaryot. Cell 9: 1251- 1261.

* cited by examiner

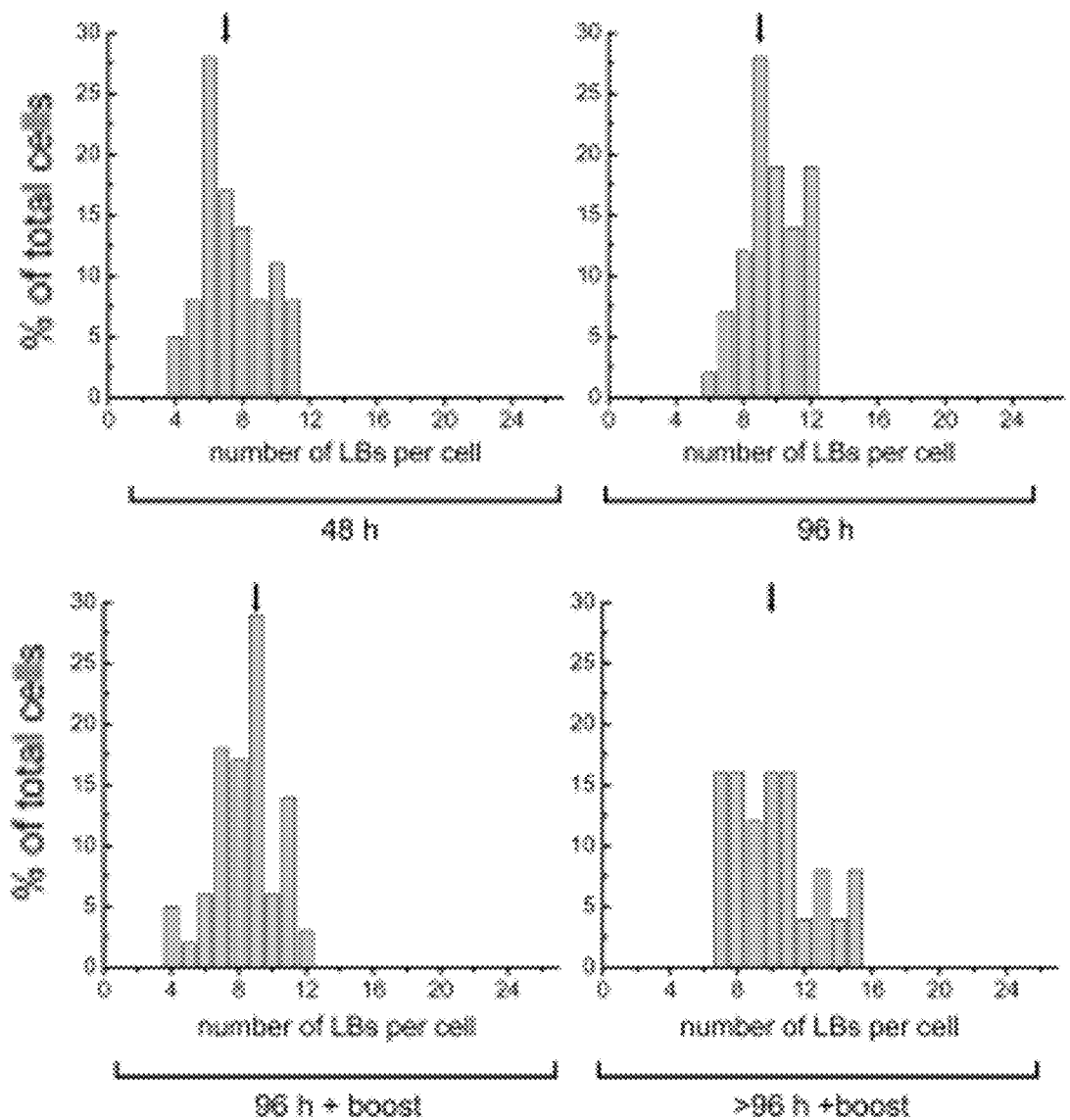

BUOYANT TRIACYLGLYCEROL-FILLED GREEN ALGAE AND METHODS THEREFOR

RELATED APPLICATIONS

This application claims priority to U.S. Provisional Patent Application 61/552,435 filed 27 Oct. 2011, which is incorporated by reference in its entirety.

GOVERNMENT SUPPORT

This work received support from a grant to the NAABB Consortium from the U.S. Department of Energy. The government may have certain rights in the invention.

INTRODUCTION

There is currently keen interest in cultivating eukaryotic algae, including microalgae, as sources of triacylglycerides (TAGs), which can be converted into biofuel such as biodiesel or jet transportation fuel (Hu, Q. et al., Plant J. 54: 621-39, 2008; Radakovits, R. et al., Eukaryot. Cell 9: 486-501, 2010; Scott, S. A., et al., Curr. Opin. Biotechnol. 21: 277-86, 2010; Wijffels, R. H. and Barbosa, M. J., Science 329: 796-9, 2010). Several laboratories have documented that the unicellular green soil alga *Chlamydamonas reinhardtii*, in response to nitrogen (N—) starvation, produces TAG-filled lipid bodies (LBs) (Wang, Z. T., et al., Eukaryot. Cell 9: 1856-68, 2009; Moellering, E. R. and Benning, C., Eukaryot. Cell 10: 97-106, 2010; Work, V. H., et al., Eukaryot. Cell 9: 1251-61, 2010; Li, Y., et al., Metab. Eng. 12: 387-91, 2010; Li, Y. et al., Biotechnol. Bioeng. 107: 258-68, 2010; Miller, R., et al., Plant Physiol. 154: 1737-52, 2010; Kropat, J., et al. Plant J. 66: 770-80, 2011; Siaut, M., et al., BMC Biotechnology, 11: 7-22, 2011; Fan, J., et al. Cell. 130: 263-79, 2011), also called lipid droplets, oil droplets, and oil bodies.

Weers et al. (Limnol. Oceanogr. 42: 1584-1589, 1997) reported that changing growth conditions to either phosphorus or nitrogen limitation caused marked changes in lipids of *C. reinhardtii*. This reference reports 30% of total, lipids that are TAG for N-starved wild type *C. reinhardtii* cells.

Wild type *C. reinhardtii* accumulates very few lipid, bodies (LBs) during its growth, phase (Wang, Z. T., et al, Eukaryot Cell 9: 1856-68, 2009), but when starved for nitrogen in stationary phase in the presence of 0.2% (33 mM) exogenous acetate, wild-type *C. reinhardtii* cells undergo a 1.5-fold increase in LB production within 48 h. Wang et al has also shown that when starch synthesis is blocked by mutation, LB production increases 30-fold, to double the wild-type levels. Furthermore, purified LB preparations prepared by the methods of Wang et al. are 90% TAG and 10% free fatty acids (FFA), and their fatty acid (FA) profiles show a mix of saturated and monounsaturated species. Wang et al. further report that the cw15 strain of *C. reinhardtii* produces ~10 ng TAG/$10^3$ cells while the cw15 sta6 strain produces ~17 ng TAG/$10^3$ cells after 18 h of N starvation. Wang et al. translated these numbers into 100 and 170 mg TGA per liter of culture at $10^7$ cells/ml. Wang et al. further speculate that since the cw15 sta6 strain of *C. reinhardtii* is expected to at least double its yield between 18 and 48 h, Wang et al. suggest that it should be possible to derive at least 340 mg of LB-derived TAG per liter of cw15 sta6 stationary-phase culture following 48 h of N starvation. Furthermore, since the LBs also include 10% FFA, which are not measured in the TAG assays, and Wang et al. presumes that LB recovery is incomplete, Wang et al. predict LB oil yield from the cw15 sta6 strain of *C. reinhardtii* can approach 400 mg per liter at $10^7$ cells/ml.

Since *C. reinhardtii* currently boasts the best-developed resources for algal molecular-genetic analysis and manipulation (Harris, E. H., *The Chlamydomonas Sourcebook. I. Introduction to Chlamydomonas and Its Laboratory Use*. Amsterdam, Elsevier, 2009), it can serve as a model organism for algal biodiesel research. Furthermore, many algal species proposed for use in biofuel production include cell walls containing algenin, which can be difficult to break (Fon Sing et al., "Production of biofuels from microalgae," in: *Mitigation and Adaptation Strategies for Global Change*, Springer, 2011). However, *Chlamydomonas* algae have no algenin.

SUMMARY

The present inventors disclose eukaryotic algal microorganisms that have triacylglycerols in amounts greater than those previously reported. Furthermore, the present inventors disclose eukaryotic algal microorganisms that are buoyant in an aqueous medium, as well as methods for producing such buoyant algae. Algae of the present teachings, including buoyant algae, can be easily harvested, and can be used, for example, to produce a biofuel such as biodiesel.

In various embodiments of the present teachings, the present inventors disclose an algal microorganism of Chlorophyta, wherein the microorganism comprises more than 50% by dry weight triacylglycerides. In various configurations, the microorganism can comprise at least 60%, by dry weight triacylglycerides, or at least 70% by dry weight triacylglycerides. In various configurations of the present teachings, a microorganism can be a Chlamydomonadales, a Chlamydomonadaceae, or a *Chlamydomonas*, such as, without limitation, a *Chlamydomonas reinhardtii*. In some embodiments, a microorganism can be buoyant in an aqueous medium. In various embodiments of the present teachings, a microorganism can be trophic for acetate. In some embodiments, a microorganism can have one or more genetic modifications (compared to wild type) whereby starch accumulation is less than that of wild type. In various embodiments, a mutation can be, without limitation, a mutation that leads to down-regulation of expression of a polypeptide of a starch biosynthesis pathway, or a mutation that leads to loss of function of a polypeptide of a starch biosynthesis pathway. In some configurations, a genetic modification can be a mutation in a gene encoding ADP-glucose pyrophosphorylase, such as a mutation in a gene encoding the small subunit of ADP-glucose pyrophosphorylase. In various configurations, a mutation can be any type of mutation, such as, without limitation, an insertion, a deletion, a missense mutation, a nonsense mutation, or an inversion, in some embodiments, a microorganism can be unable to synthesize starch, or any detectable amount of starch. In some embodiments, a microorganism can be of an algal species that lacks algenin.

In various embodiments, the present teachings include cell cultures. A cell culture of the present teaching can comprise a culture medium, and a plurality of eukaryotic microorganisms classifiable as Chlorophyta, Chlamydomonadales, Chlamydomonadaceae and/or *Chlamydomonas*. In some configurations, the microorganisms can be *Chlamydomonas reinhardtii*. In some configurations, the culture medium can comprise an acetate, such as, without limitation, potassium acetate, which can be 20 mM potassium acetate. In some configurations, the culture medium can comprise an acetate, but lack a nitrogen source. In some configurations, microorganisms of a culture of the present teachings can be deficient in starch production, compared to wild type. In some configurations, microorganisms of a culture of the present teachings can comprise at least one mutation in a gene of a starch biosynthetic pathway. In these microorganisms, starch accumulation can be less than that of wild-type. In some configurations, the at least one mutation can be a mutation of a gene encoding ADP-glucose pyrophosphorylase, such as a gene encoding the small subunit of ADP-glucose pyrophosphorylase. In some configurations, microorganisms of these embodiments can synthesize no starch. In some configurations, microorganisms of these embodiments can accumulate no starch. In some configurations, a cell culture of the present teachings can comprise microorganisms that are buoyant.

In various embodiments, a culture of eukaryotic algal, microorganisms of the present teachings can comprise a plurality of microorganisms of order Chlamydomonadales, and a culture medium, wherein the culture comprises greater than 340 mg/l triacylglycerols. In some configurations, a culture can comprise at least 360 mg/l triacylglycerols, at least 400 mg/l triacylglycerols, greater than 400 mg/l triacylglycerols, at least 500 mg/l triacylglycerols, at least 600 mg/l triacylglycerols, at least 700 mg/l triacylglycerols, at least 800 mg/l triacylglycerols, at least 900 mg/l triacylglycerols, at least 1,000 mg/l triacylglycerols, at least 1,100 mg/l triacylglycerols, at least 1,200 mg/l triacylglycerols, or at least 1,300 mg/l triacylglycerols. In some embodiments, triacylglycerol content of a culture can comprise, consist essentially of, or consist of up to 1,000 mg/l triacylglycerols, up to 1,100 mg/l triacylglycerols, up to 1,200 mg/l triacylglycerols, up to 1,300 mg/l triacylglycerols or up to 1,400 mg/l triacylglycerols. In various embodiments, a culture can comprise buoyant microorganisms, such as, without limitation, buoyant *Chlamydomonas reinhardtii* that do not make starch and harbor one or more mutations in a gene of a starch biosynthetic pathway, in various configurations, such microorganisms can accumulate less starch than wild type. In some configurations, a culture can comprise microorganisms that do not synthesize starch. In some configurations, a culture can comprise microorganisms that do not accumulate starch. In some configurations, a mutation can be in a gene encoding ADP-glucose pyrophosphorylase. In some configurations, a mutation can be in a gene encoding the small subunit of ADP-glucose pyrophosphorylase.

In various embodiments, the present teachings include methods of forming a culture of buoyant microorganisms, and methods of forming a culture of microorganisms comprising triacylglycerols at a concentration greater than 340 mg/l. These methods include: i) providing at least one microorganism of order Chlamydomonadales; ii) growing the at least one microorganism to log phase in a first aqueous medium comprising a) at least one nitrogen source and b) at least one acetate, thereby forming a plurality of microorganisms; iii) replacing the first aqueous medium with a second aqueous medium, wherein the second aqueous medium comprises at least, one acetate but lacks a nitrogen source; iv) growing the plurality of microorganisms in the second aqueous medium; v) at 1 day, about 1 day, 2 days, about 2 days, 3 days, about 3 days, 4 days or about 4 days after replacing the first aqueous medium with the second aqueous medium, supplementing the second aqueous medium with additional acetate; and vi) growing the plurality of microorganisms in the acetate-supplemented second medium.

In some embodiments, the present teachings include methods of forming a culture comprising microorganisms and greater than 340 mg/l triacylglycerides. In various configurations, these methods can comprise, in order: i) providing a population of microorganisms of order Chlamydomonadales growing at log phase in a first aqueous medium comprising a) at least one nitrogen source and b) at least one acetate; ii) replacing the first aqueous medium with a second aqueous medium, wherein the second aqueous medium comprises at least one acetate but lacks a nitrogen source; iii) growing the population of microorganisms in the second aqueous medium; iv) at 1 day, about 1 day, 2 days, about 2 days, 3 days, about 3 days, 4 days or about 4 days after replacing the first aqueous medium with the second aqueous medium, supplementing the second aqueous medium with additional acetate; and v) growing the population of microorganisms for at least about 2 days after supplementing the second aqueous medium with additional acetate, whereby the culture comprises greater than 340 mg/l TAG.

In various configurations, the at least one microorganism can be grown to log phase in the first aqueous medium comprising an acetate and a nitrogen source such as, for example, $NH_4Cl$ for 1 day, for about 1 day, for 2 days, for about 2 days, for 3 days, for about 3 days, for 4 days, for about 4 days, or longer before replacing the first aqueous medium with a second aqueous medium that comprises acetate but no nitrogen source.

In various configurations, the second aqueous medium can be supplemented with additional acetate at 1 day, about 1 day, 2 days, about 2 days, 3 days, about 3 days, 4 days, or about 4 days after the first aqueous medium is replaced with the second aqueous medium. In various configurations, the growing the plurality of microorganisms in the acetate-supplemented second medium can comprise growing the microorganisms for at least 2 days, for about 2 days, for 3 days, for about 3 days, for 4 days, for about 4 days, for 5 days, for about 5 days, for 6 days, for about 6 days, for 7 days, for about 7 days, for 8 days, for about 8 days, for 9 days, for about 9 days, or longer in the acetate-supplemented medium, so that, the microorganisms can be growing in a medium lacking a nitrogen source for 4 days, about 4 days, for 5 days, for about 5 days, for 6 days, for about 6 days, for 7 days, for about 7 days, for 8 days, for about 8 days, for 9 days, for about 9 days, for 10 days, for about 10 days, for 11 days, for about 11 days, or longer. In various configurations, the microorganisms can be a *Chlamydomonas*, such as a *Chlamydomonas reinhardtii*. In various configurations, the microorganisms can comprise at least one mutation in a starch synthesis pathway. In various configurations, the microorganisms do not accumulate or synthesize starch. In various configurations, a culture of the present teachings can reach a TAG content greater than 340 mg/l (without concentrating the medium) starting about 4 days after replacing the first medium with the second medium, which can be, for example, at about 2 days after supplementing the second medium with acetate, in various configurations, cultures can reach a TAG content greater than 340 mg/l at about 5 days, about 6 days, about 7 days, about 8 days, about 9 days, about 10 days, about 11 days, or about 12 days after cells are placed in a medium lacking a nitrogen source, provided that the culture medium is supplemented with additional acetate. In various configurations, cultures formed by the methods of the present teachings can comprise at least 400 mg/l triacylglycerols, greater than 400 mg/l triacylglycerols, at least 500 mg/l triacylglycerols, at least 600 mg/l triacylglycerols, at least 700 mg/l triacylglycerols, at least 800 mg/l triacylglycerols, at least 900 mg/l triacylglycerols, at least 1,000 mg/l triacylglycerols, at least 1,100 mg/l triacylglycerols, at least 1,200 mg/l triacylglycerols, at least 1,300 mg/l triacylglycerols, up to 900 mg/l triacylglycerols, up to 1,000 mg/ml triacylglycerols, up to 1,100 mg/ml triacylglycerols, up to 1,200 mg/ml triacylglycerols, up to 1,300 mg/ml triacylglycerols, or up to 1,400 mg/ml triacylglycerols. In various configurations, the second aqueous medium can comprise from about 10 to about 50 mM acetate, such as 20 mM acetate or about 20 mM acetate, such as, for example 20 mM potassium acetate or about 20 mM potassium acetate. In various configurations, after supplementing the second aqueous medium with additional acetate, the medium can comprise up to about 40 mM acetate, up to about 50 mM acetate, or greater. In various configurations, the microorganisms can be buoyant.

In some embodiments, the present inventors disclose methods of forming a biofuel. In various configurations, these methods comprise growing a culture of eukaryotic microorganisms as described herein, and harvesting the microorganisms from the culture, wherein the culture contains TAG greater than 340 mg/l, at least 400 mg/l triacylglycerols, greater than 400 mg/l triacylglycerols, at least 500 mg/l triacylglycerols, at least 600 mg/l triacylglycerols, at least 700 mg/l triacylglycerols, at least 800 mg/l triacylglycerols, at least 900 mg/l triacylglycerols, at least 1,000 mg/l triacylglycerols, at least 1,100 mg/l triacylglycerols, at least 1200 mg/l triacylglycerols, at least 1300 mg/l triacylglycerols, up to 900 mg/l triacylglycerols, up to 1,000 mg/ml triacylglycerols, up to 1,100 mg/ml triacylglycerols, up to 1,200 mg/ml triacylglycerols, up to 1,300 mg/ml triacylglycerols, or up to 1,400 mg/ml triacylglycerols. In some configurations, the microorganisms can be buoyant microorganisms. In some configurations, buoyant microorganisms can be harvested, by collecting floating cells from a culture. In various configurations, the TAG can be released from the cells using methods well known to skilled artisans. Biofuels, such as biodiesel, can be generated with the TAG using methods well known to skilled artisans (see, e.g., Halim, R., Bioresource Technology 102:178-185, 2011).

BRIEF DESCRIPTION OF THE DRAWINGS

FIG. 6A illustrates STA6 cells that were N starved for 48 h, 96 h 96 h with an acetate boost, and >96 h with an acetate boost.

DETAILED DESCRIPTION

Figure 1A:
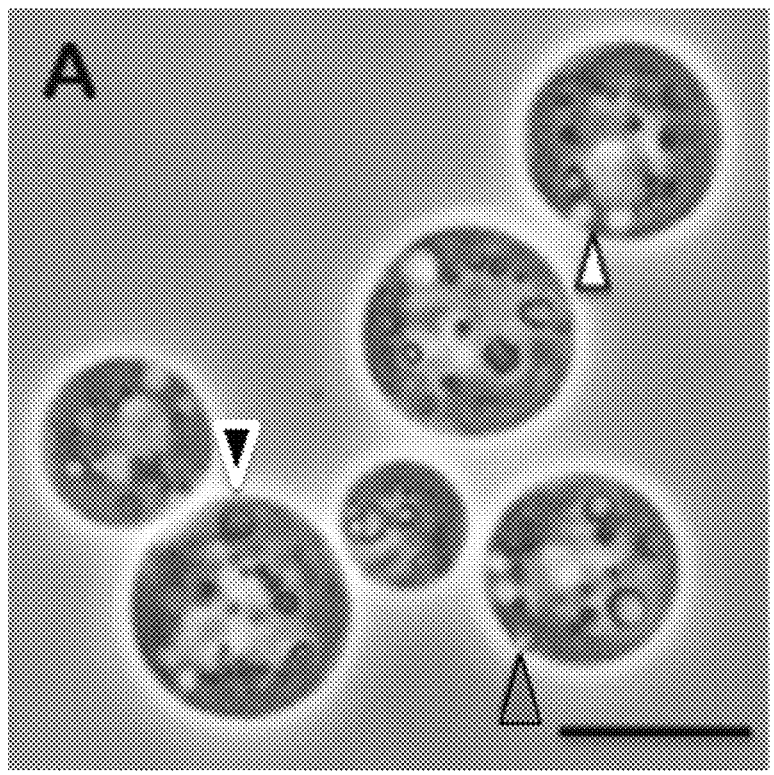
FIG. 1A illustrates sta6 cells in mid-log phase.

The present inventors disclose cells, cell cultures, and methods of producing cell cultures comprising eukaryotic algae which produce triacylglycerols (TAG) in amounts greater than previously reported. The present inventors have developed conditions conducive to LB formation. In various embodiments, they found that N-stress-induced LB formation can be acetate dependent in the STA6 and sta6 strains (FIG. 2C), as reported for the STA6 strain using TAG quantification (Fan, J., et al., FEBS Lett, 585:1985-1991, 2011).

In some embodiments, sta6, a starch-null mutant strain of *Chlamydomonas reinhardtii*, were compared and analyzed cells in log and stationary phase, in various stages of N-starvation in both liquid media and on agar plates, and in maturing zygotes. The influence of exogenous acetate and lighten lipid body (LB) formation was assessed. Light and deep-etch electron microscopy were used, to visualize triacylglyceride (TAG)-filled lipid bodies (LBs) of the green eukaryotic alga *Chlamydomonas reinhardtii*, a model organism for biodiesel research.

The present inventors observed that cells in nitrogen (N)-replete media contain small cytoplasmic lipid bodies (α-cyto-LBs) and small chloroplast plastoglobules. However, when they starve the cells for nitrogen by transferring them, to a medium comprising acetate but no source of nitrogen, they observe that β-cyto-LB formation is massively stimulated. β-Cyto-LBs are LBs that are in intimate association with the endoplasmic reticulum (ER) and the outer membrane of the chloroplast envelope. When cells blocked in blocked in starch biosynthesis, such as sta6 mutant cells of *Chlamydomonas reinhardtii*, are N-starved, they produce β-cyto-LBs and also chloroplast LBs (cpst-LBs) that are much larger than plastoglobules and eventually engorge the chloroplast stroma. The inventors found that production of β-cyto-LBs and cpst-LBs can be dependent on exogenous acetate and can be inhibited by darkness. Without being limited by theory, the present inventors hypothesized that the greater LB yield reported for N-starved sta6 cells can be attributed to their ability to produce cpst-LBs. Provision of an "acetate boost" during N-starvation generates sta6 cells that become so engorged with LBs—at the expense of cytoplasm and most organelles—that they can float on water even when centrifuged. This property can be a desirable feature for algal harvesting during biodiesel production.

Methods and compositions described herein utilize laboratory techniques well known to skilled artisans. Such techniques can be found in laboratory manuals such as Sambrook, I., et al, Molecular Cloning: A Laboratory Manual, 3rd ed. Cold Spring Harbor Laboratory Press, Cold Spring Harbor, N.Y., 2001; Spector, D. L. et al. Cells: A Laboratory Manual, Cold Spring Harbor Laboratory Press, Cold Spring Harbor, N.Y., 1998; Harris, E. H., The *Chlamydomonas* Sourcebook: A Comprehensive Guide to Biology and Laboratory Use, Academic Press, Maryland Heights, Mo., 2008. In addition, the present teachings including the examples set forth herein may make use of the following materials and methods.

TAP Medium.

To make TAP medium the following three stock solutions need to be prepared.

Stock Solutions:

1. TAP salts

| | |
|---|---|
| $NH_4Cl$ | 15.0 g |
| $MgSO_4 \cdot 7H_2O$ | 4.0 g |
| $CaCl_2 \cdot 2H_2O$ | 2.0 g |
| water to 1 liter | |

2. Phosphate solution

| | |
|---|---|
| $K_2HPO_4$ | 28.8 g |
| $KH_2PO_4$ | 14.4 g |
| water to 100 ml | |

3. Rutner's trace elements

For 1 liter final mix, dissolve each compound in the volume of water indicated. The EDTA should be dissolved in boiling water, and the $FeSO_4$ should be prepared last to avoid oxidation.

| compound | amount | water |
|---|---|---|
| EDTA disodium salt | 50 g | 250 ml |
| $ZnSO_4 \cdot 7 H_2O$ | 22 g | 100 ml |
| $H_3BO_3$ | 11.4 g | 200 ml |
| $MnCl_2 \cdot 4 H_2O$ | 5.06 g | 50 ml |
| $CoCl_2 \cdot 6 H_2O$ | 1.61 g | 50 ml |
| $CuSO_4 \cdot 5 H_2O$ | 1.57 g | 50 ml |
| $(NH_4)_6Mo_7O_{24} \cdot 4 H_2O$ | 1.10 g | 50 ml |
| $FeSO_4 \cdot 7 H_2O$ | 4.99 g | 50 ml |

Mix all solutions except EDTA. Bring to boil, then add EDTA solution. The mixture should turn green. When everything is dissolved, cool to 70° C. Keeping temperature at 70° C. add 85 ml hot 20% KOH solution (20 grams/100 ml final volume). Do NOT use NaOH to adjust the pH.

Bring the final solution to 3 liter total volume, it should be clear green initially. Stopper the flask with a cotton plug and let it stand for 1-2 weeks, shaking it once a day. The solution should eventually turn purple and leave a rust-brown precipitate, which can be removed by filtering through two layers of Whatman#1 filter paper, repeating the filtration if necessary until the solution is clear. Store refrigerated or frozen convenient aliquots. The time for formation of the precipitate maybe shortened by bubbling the solution with filtered air.

If no precipitate forms, the solution is still usable. However, the pH needs to be checked and adjust it to around 7.0 using either KOH or HCl as needed.

To prepare sulfur-free trace elements for hydrogen generation, the sulfate salts can be replaced with equimolar chloride salts ($ZnCl_2$ 10.0 g; $CuCl_2 \cdot 2H_2O$ 1.00 g; $FeCl_2 \cdot 4H_2O$, 3.60 g).

To make the final TAP medium, mix the following:

2.42 g Tris
25 ml solution #1 (salts)
0.375 ml solution #2 (phosphate)
1.0 ml solution #3 (trace elements)
1.0 ml glacial acetic acid
water to 1 liter For solid medium, add 15 g agar per liter.

Microbial cells can be transformed using a variety of standard techniques known in the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual 3d ed., Cold Spring Harbor Laboratory Press, ISBN-10: 0879695773; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

Strains and Culture Conditions

Most experiments were conducted with the nonarginine-requiring STA6 strain CC-4349 and the sta6 strain CC-4348 (*Chlamydomonas* Center). Complemented sta6 strains C2, C4, and C6 were kindly provided by David Dauvillée and Steven Ball (CNRS, Villeneuve d'Asq, France). Zygotes were the product of matings between wild-type (wt) CC-125 and CC-621. Wild-type *C. reinhardtii* has cell walls and flagella; the STA6 strain lacks both flagella and cell walls but engages in normal starch biosynthesis; the sta6 strain, derived from the parental STA6 strain by insertional mutagenesis, is wall-less, flagella-less, carries a deletion of the STA6 gene encoding the small subunit of ADP-glucose pyrophosphorylase (Zahawinski, C., et al., Bacteriol. 183: 1069-77, 2001), and synthesizes no detectable starch (Work, V. H., et al., Eukaryot. Cell 9: 1251-61, 2010, and our DEEM observations). However, in various embodiments of the present teachings, methods for producing cultures comprising greater than 340 mg/l triacylglycerols or for producing buoyant microorganisms do not rely on using microorganisms lacking flagella and/or cell walls.

Liquid cultures (75 ml in 150-ml Erlenmeyer flasks) were grown in phosphate-buffered high-salt medium (HSM) (Sueoka, N., Proc. Natl. Acad. Sci. USA. 46: 83-91, 1960) containing 9.3 mM $NH_4Cl$ as a nitrogen source and supplemented with 20 mM potassium acetate. Flasks were rotated at 125 rpm at 30 μE illumination from daylight fluorescent bulbs. Plate-grown cells were maintained out to 30 days on TAP (Gorman, D. S. and Levine, R. P., Proc. Natl. Acad. Sci. USA. 54: 1665-9, 1965) medium supplemented with 1.5% agar (Fluka; Sigma-Aldrich Chemical, St, Louis, Mo.). Zygotes were matured on N-free TAP plates. Cells were inoculated from plates and grown to log phase (mean hemacytomer count of 44 cultures: $2.5 \times 10^6$ cells/nil), pelleted at 800×g and resuspended in 75 ml HSM+20 mM acetate and lacking $NH_4Cl$. In some experiments, 1 ml of 1.5 M K acetate was added to cultures that had been N-starved for 2 days (the 20 mM "acetate boost"). In some configurations, the pH of HSM+acetate can be 7.0 and can rise to 8-8.5 after 5 days N-starvation with acetate boost.

Microscopy

For light microscopy, 750 μl of cell culture was pelleted at 800×g and brought up in 15 μl of its own supernatant to generate dense fields of cells for photography (a procedure not possible for obese cells; hence their images are more dispersed). Cells were examined and photographed using a Wild M20 phase/bright field microscope with a 40× objective, a 1.25× Variomag, and 2.5× camera adapter (Canon EOS Rebel XTi). All fields were photographed at the same magnification. Calculations of LBs/cell (FIG. 6) were made using micrographs of "popped cells" or intact cells that were sufficiently dry that, their LB content could be readily scored. >2000 light micrographs from 72 independent samples were examined for this study.

For electron microscopy, live cells were pelleted at 800×g, or scraped from agar plates. Obese cells were recovered from the meniscus after centrifugation. Cells were layered, onto cushioning material and dropped onto the surface of a helium cooled copper block, fractured, etched, and replicated using the protocols and apparati developed by Heuser (Heuser, J. E., J. Elect. Microsc. 60: S3-S29, 2011). >2000 DEEM micrographs from 48 independent samples were examined for this study.

EXAMPLES

The following examples are illustrative of various embodiments of the present teachings and are not intended to limit the scope of any claim. Persons of skill in the art will recognize that many variations are possible that are within the scope of the present teachings.

Example 1

This example illustrates the analysis of LB formation in *C. reinhardtii* using phase contrast and bright-field light microscopy of living cells and deep-etch electron microscopy (DEEM) of quick-frozen living cells.

FIGS. 1-5 present montages of living STA6 and sta6 cells visualized by phase contrast and bright-field (FIG. 4) microscopy, all photographed and printed at the same magnification. The immotile cells settle onto the glass slide without fixation and they flatten out as they dry, permitting high-resolution images. Eventually they "pop" when the plasma membrane lyses (Wang, Z. T., et al, Eukaryot Cell 9: 1856-68, 2009), depositing their starch and LBs (STA6) or their LBs (sta6) in situ on the slide. The two contractile vacuoles continue to pump until a cell pops, indicating that the cells are still operant during the drying process.

Example 2

This example illustrates nitrogen, starvation of cells for two days from log phase.

Figure 1B:
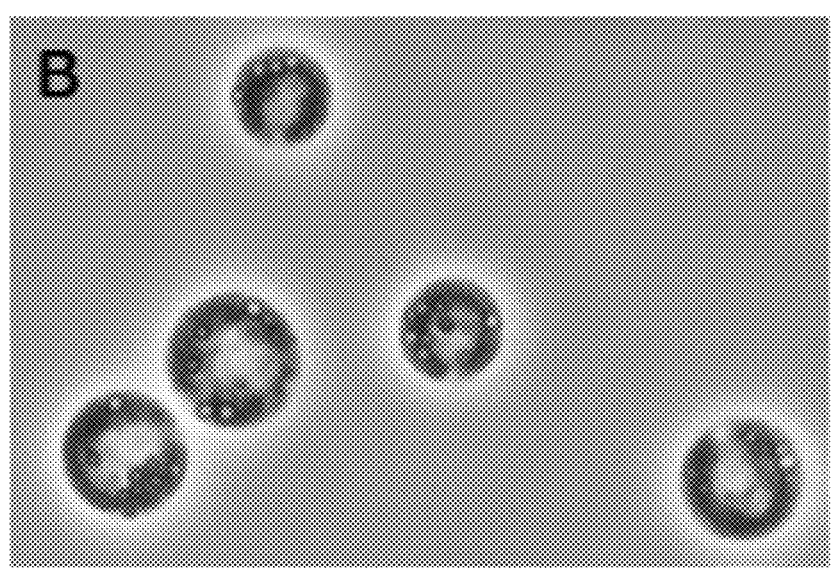
FIG. 1B illustrates sta6 cells after 1 day of N-starvation.
Figure 1C:
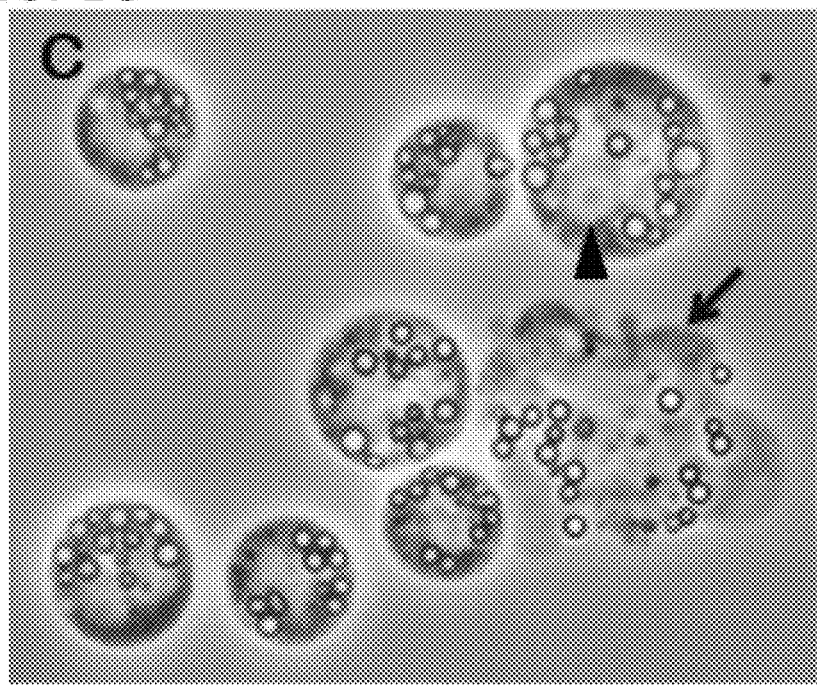
FIG. 1C illustrates sta6 cells after 2 days of N-starvation.
Figure 1D:
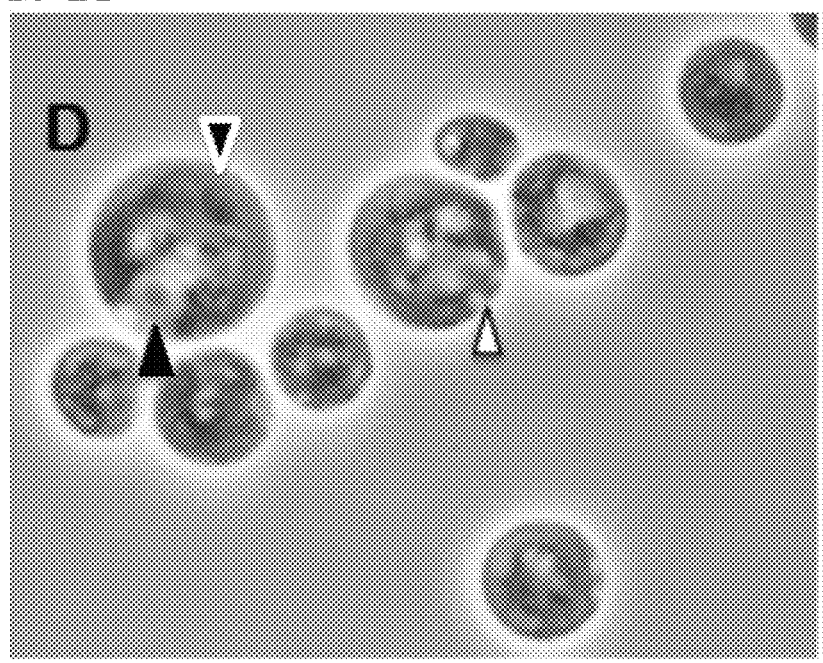
FIG. 1D illustrates STA6 cells in log-phase.
Figure 1E:
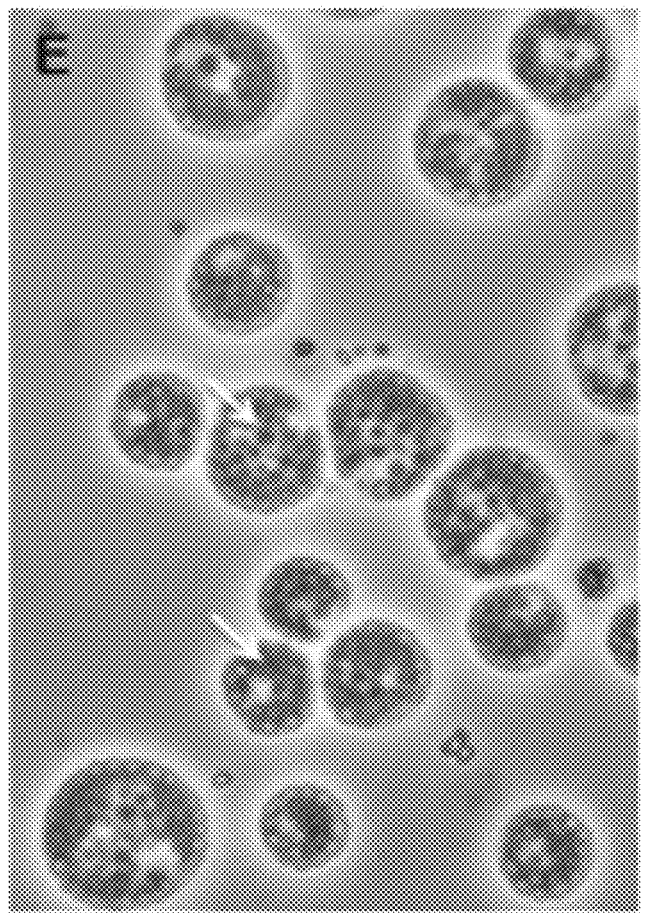
FIG. 1E illustrates STA6 cells after 2 days of N-starvation.
Figure 1F:
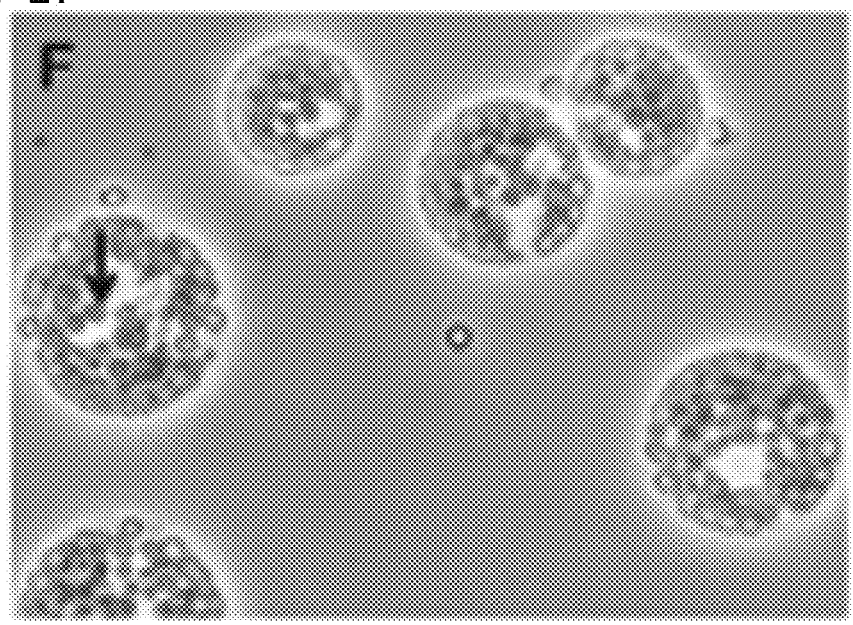
FIG. 1F illustrates sta6 cells complemented with a STA6 transgene.

FIG. 1A shows sta6 cells in mid-log phase ($2-3 \times 10^6$ cells/ml); FIG. 1B shows sta6 after 1 day of N-starvation from log-phase in HSM+20 mM acetate; and FIG. 1C show sta6 cells after 2 days N-starvation. In these experiments, the cultures increase in cell number after transfer to N-free medium, stabilizing at $0.8-1 \times 10^7$. As used herein, "transfer to N-free medium" means that cells are transferred to a medium lacking a nitrogen source; however, this does not exclude the possibility that a small, residual amount of nitrogen source (e.g., $NH_4Cl$ from a previous medium remains in the medium with, the cells, FIG. 1D shows STA6 in log-phase; FIG. 1E shows STA6 cells that were N starved, for 2 days; and FIG. 1F shows sta6 cells complemented with a STA6 transgene. Black arrowheads point out nuclei with central nucleoli; white arrowhead point out contractile vacuole(s); Gray arrowhead outlined in black point out eyespot (refracts blue with phase optics); Black arrowheads with white outline point out pyrenoids. Black arrow indicates a popped cell in FIG. 1C, white arrows indicate interior LBs in FIG. 1E and black arrow indicates starch in white at the periphery in FIG. 1F. All micrographs at same magnification as FIG. A; scale bar in FIG. 1A=10 μm.

Round luminous LBs are just visible in 1-day N-starved cells (FIG. 1B) and conspicuous in 2-day N-starved sta6 cells (FIG. 1C). Included in FIG. 1C (arrow) is a popped cell (Wang, Z. T., et al., Eukaryot. Cell 9: 1856-68, 2009) displaying its LB content. A time course of 2-day N-starved popping cells illustrates several important features of the popping process in live cells: when the cell membrane lyses, the LBs neither fragment nor fuse, nor do they change in size when they adsorb to the glass slide.

The STA6 cells make little starch during growth (FIG. 1D), but during the first two days of N-starvation they produce abundant starch (Work, V. H., et al. Eukaryot. Cell 9: 1251-61, 2010; Siaut, M., et al., BMC Biotechnology. 11: 7-22, 2011), visible in FIG. 1E as a rim of refractile granules around each cell perimeter and as brown punctate material, in the cell interior. Larger brown LBs also form in the cell interior (FIG. 1E, arrows). Because starch accumulation obscures LB profiles, most of the light-microscope images in this report show sta6 cells.

Example 3

This example illustrates N-starving cells from log versus stationary phase.

Figure 2A:
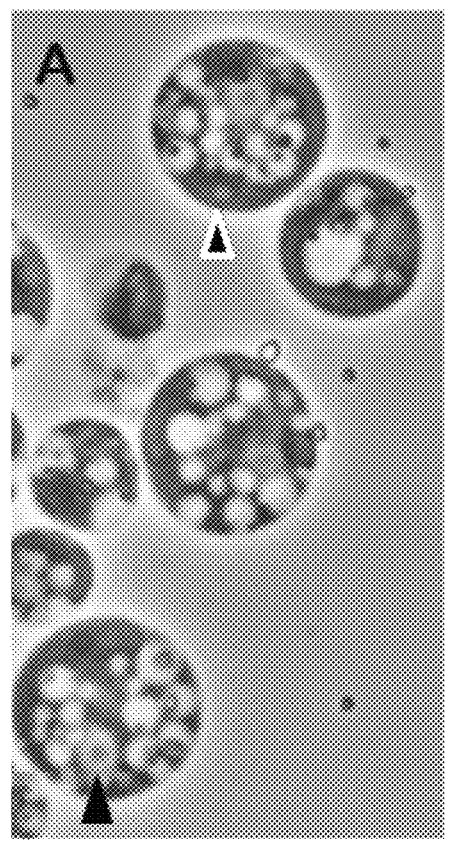
FIG. 2A illustrates sta6 cells in stationary phase.
Figure 2B:
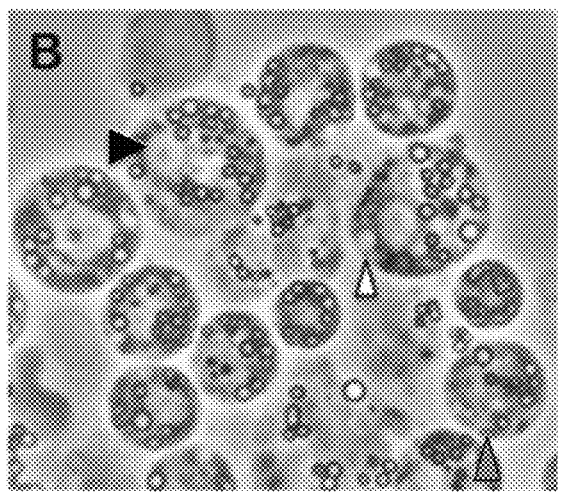
FIG. 2B illustrates sta6 cells N-starved from stationary phase for 2 days.

In a previous report (Wang, Z. T., et al., Eukaryot, Cell 9: 1856-68, 2009), cells were N-starved after entering stationary phase (~1-2×10$^7$ cells/ml). The present inventors have found that STA6 and sta6 cells undergo an extensive autophagocytic program when they enter stationary phase, manifest in FIG. 2A as large populations of cytoplasmic vacuoles containing polyphosphate grannies (derived from organelles called acidocalcisomes (Ruis, F. A., et al., J. Biol. Chem. 276: 46196-203, 2001; Docampo, R., et al., Phil. Trans. R. Soc. B. 365: 775-84, 2010). Stationary-phase cells produce smaller LBs after 2 days of N-starvation (compare FIGS. 1C and 2B); moreover, they become moribund and tend to lyse (FIG. 2B). Therefore, most of the images in this report depict cells N-starved from log phase. FIG. 2A shows sta6 cells in stationary phase. Vacuoles in interior often contain polyphosphate granules. FIG. 2B shows sta6 cells N-starved from stationary phase for 2 days. The field includes many lysed cells. Black arrowheads point out nuclei with central nucleoli; white arrowhead point out contractile vacuole(s); Gray arrowhead outlined in black point out eyespot (refracts blue with phase optics); Black arrowheads with white outline point out pyrenoids.

Example 4

This example illustrates N-starving cells in the light without acetate.

Figure 2C:
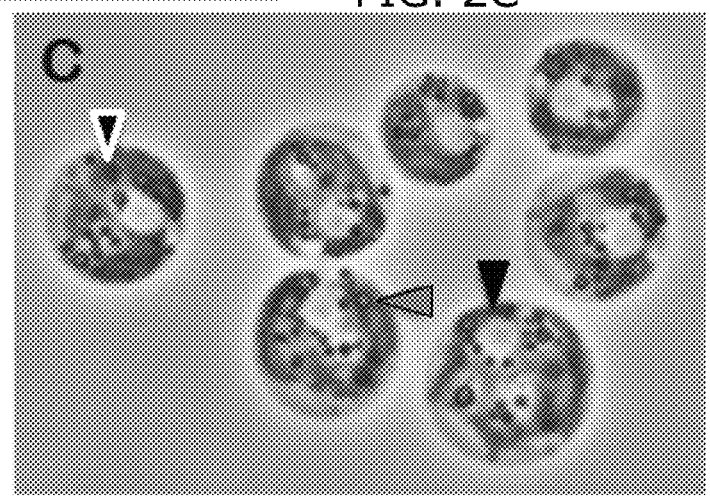
FIG. 2C illustrates sta6 cells N-starved in the light without acetate for 2 days.

FIG. 2C shows sta6 cells that were N-starved in the light for 2 days without acetate. FIG. 2C shows sta6 cells that were N starved in the light for 2 days without acetate. The omission of acetate prevents the accumulation of any visible LBs in both the sta6 strain and the STA6 strain, although there is no inhibitory effect on starch accumulation (Martin, N. C., and U. W. Goodenough, J. Cell Biol. 67:587-605, 1975). When the acetate-free cells are provided with 20 mM acetate after 2 days, they engage in robust LB formation during the following 2 days.

Example 5

Figure 2D:
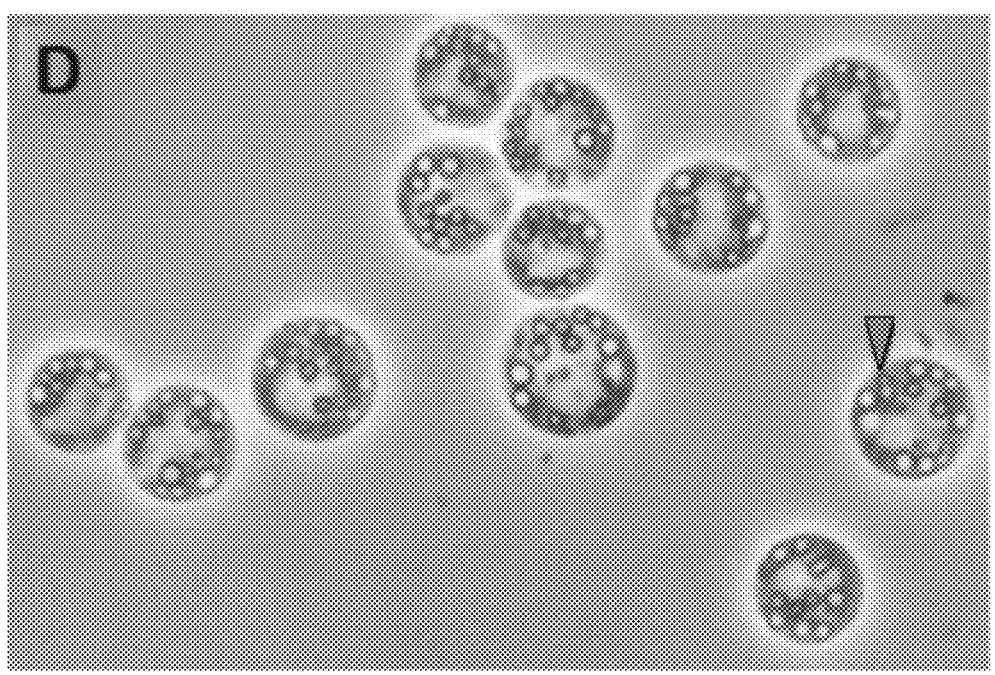
FIG. 2D illustrates sta6 cells grown in the light without acetate for 2 days then transferred in log phase.

This example illustrates N starvation of cultures grown in the absence of acetate. While both strains require exogenous acetate for N-stress-induced LB formation under the conditions employed, it is not necessary that the cells be cultivated in the presence of acetate. FIG. 2D shows sta6 cells that were grown in the light in acetate-free HSM and then transferred in log phase to acetate-containing, N-free HSM for 2 days. LB levels are comparable to those in cells that were grown in acetate-containing medium (FIG. 1C).

Example 6

This example illustrates long-term maintenance of N-starved sta6 cells and effects of an acetate boost.

FIG. 3A shows sta6 cells nitrogen starved, in acetate from log phase for 4 days. LB size increased compared with that in 2-day cells (FIG. 1C), but when such cells were incubated for more than 4 days, they became moribund and lysed.

However, when sta6 cells were given an additional. 20 mM acetate (from a concentrated stock) after a 2-day N starvation in 20 mM acetate, they remained viable up to 2 weeks, and their LBs continued to enlarge. An acetate boost also enhanced the LB size of sta6 cells first grown to log phase in minimal medium.

Example 7

This example illustrates long-term-maintenance of N-starved sta6 cells and effects of an "acetate boost".

Figure 3:
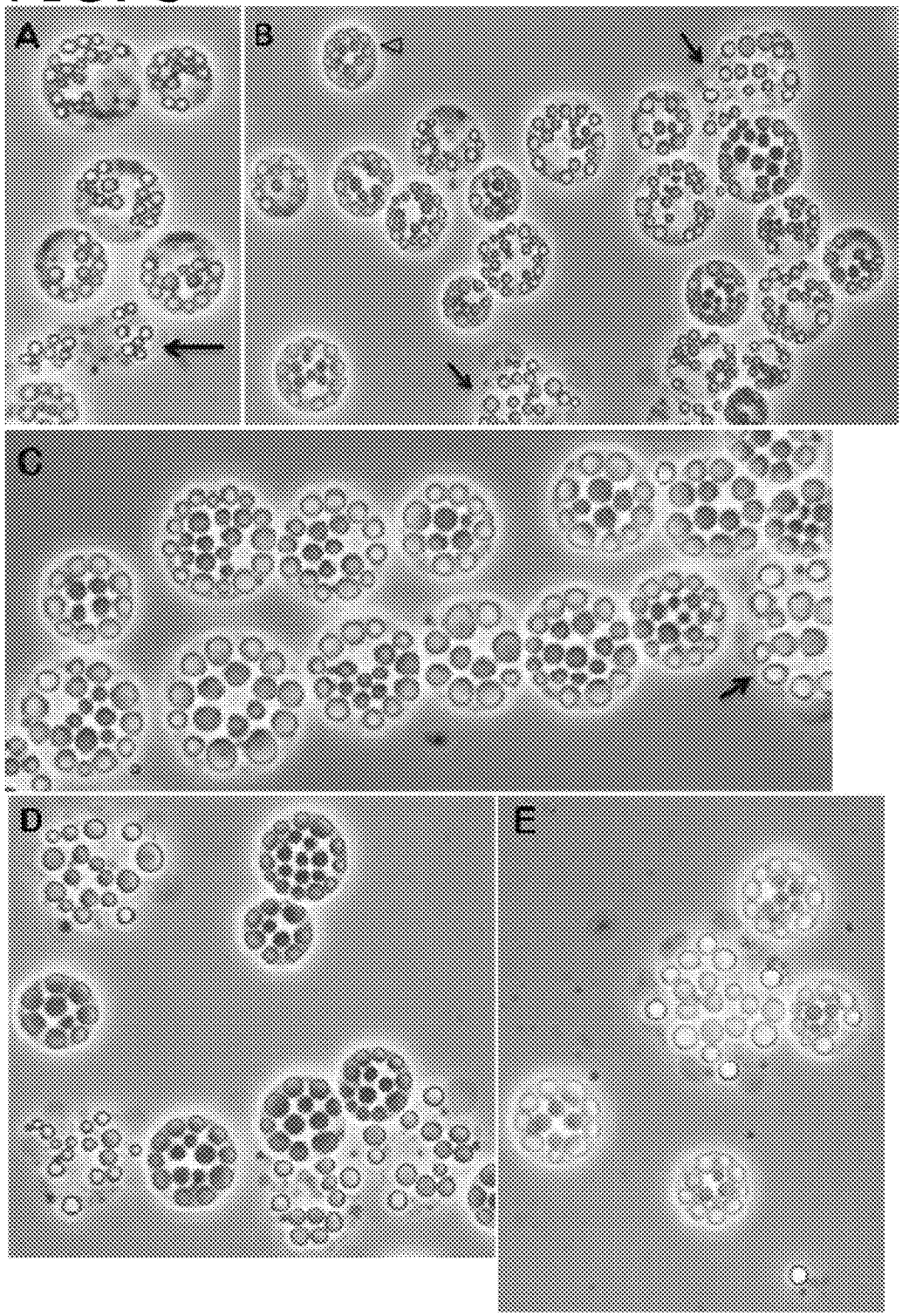
FIG. 3A illustrates sta6 cells nitrogen starved for 4 days without acetate boost.
FIG. 3B illustrates sta6 cells nitrogen starved with an acetate boost for 4 days.
FIG. 3C illustrates sta6 cells nitrogen starved with an acetate boost for 6 days.
FIG. 3D illustrates sta6 cells nitrogen starved with an acetate boost for 8 days.
FIG. 3E illustrates sta6 cells nitrogen starved with an acetate boost for 10 days.

FIG. 3 shows sta6 cells that were nitrogen starved, for 4 days without acetate boost (A) or nitrogen starved with an acetate boost for 4 days (B), 6 days (C), 8 days (D; note the four popped cells), or 10 days (E; note the popped cell). Arrows indicate popped cells. The magnification is the same as in FIG. 1.

FIG. 3A shows sta6 cells N-starved in acetate from log phase for 4 days. LB size has increased compared with 2-day cells (FIG. 1C), but when such cells are incubated for more than 4 days, they become moribund and lyse. If however, sta6 cells are given an additional 20 mM acetate (from a concentrated stock) after a 2-day N-starvation in 20 mM acetate, such 4-day "acetate-boosted" cells (FIG. 3B) remain viable out to 2 weeks, and their LBs continue to enlarge. An acetate boost also enhances the LB size of sta6 cells first grown to log phase in minimal medium.

FIG. 3B-E show N-starved acetate-boosted sta6 cells after 4, 6, 8, and 10 days of culture. The LBs greatly increased in size with continued, incubation. This size increase is also evident, in "popped" fields, and in bright-field images (FIGS. 4A-D), where LBs increasingly fill the cells until the cells appear "stuffed." These cells are designated as obese.

When observed by phase contrast, the LBs of obese sta6 cells are lighter in color at the cell perimeter than in the interior (FIG. 3). As documented with DEEM (later sections), the LBs at the perimeter are located in the peripheral chloroplast (cpst-LBs) while those in the interior are located in the cytoplasm (β-cyto-LBs). The color differential is lost when the sta6 cells pop (FIGS. 3D and E), indicating that it is a phase-optics effect.

Figure 4:
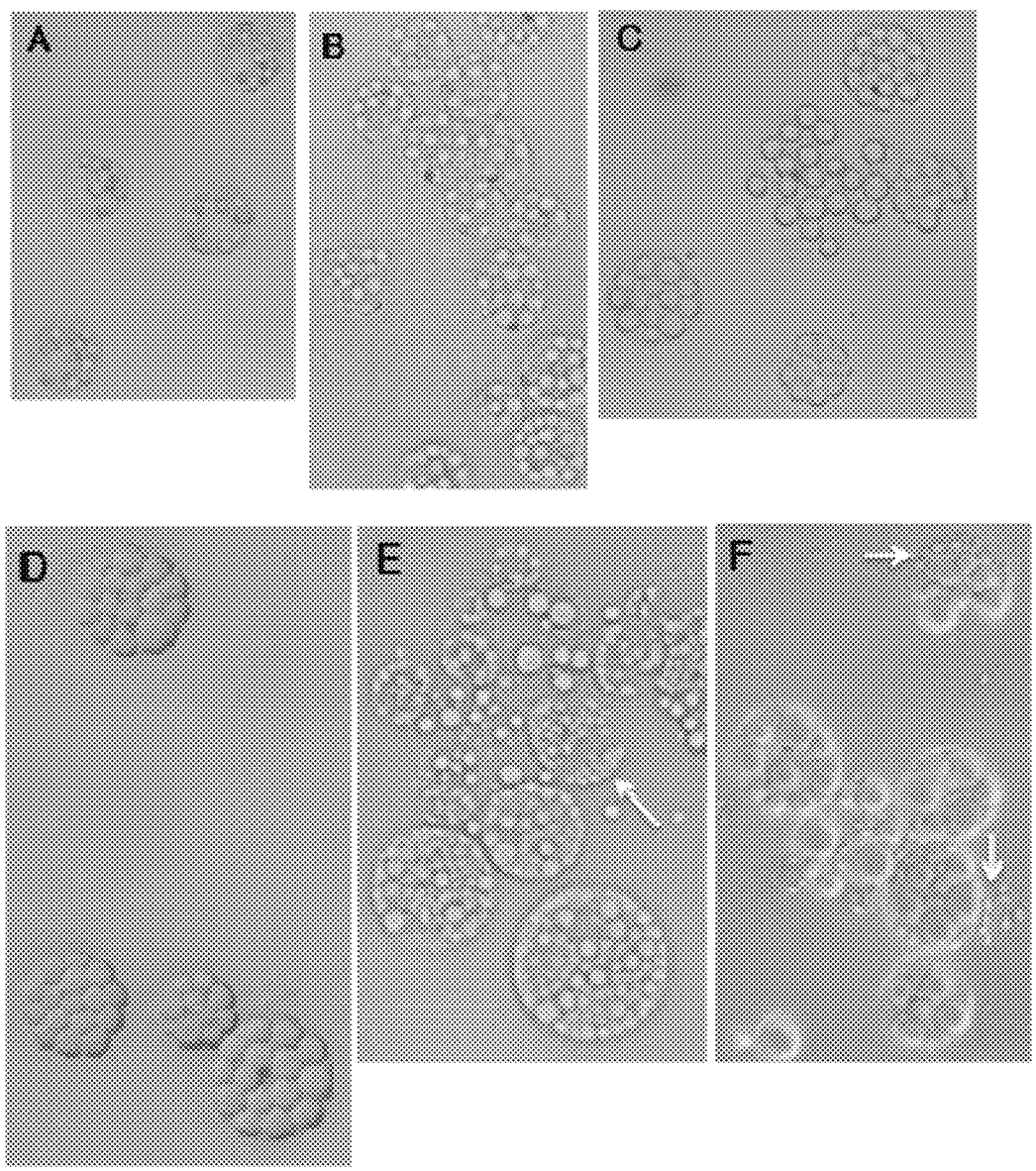
FIG. 4A illustrates sta6 cells N-starved for 2 days.
FIG. 4B illustrates sta6 cells N-starved with an acetate boost for 4 days.
FIG. 4C illustrates sta6 cells N-starved with an acetate boost for 10 days.
FIG. 4D illustrates sta6 cells N-starved with an acetate boost for 14 days.
FIG. 4E illustrates STA6 cells N-starved with an acetate boost for 4 days.
FIG. 4F illustrates STA6 cells N-starved with an acetate boost for 14 days.

FIG. 4 show bright-field images of N-starved cell Eyespots are darker. sta6 cells were N starved for 2 days (A) or N starved with an acetate boost for 4 days (B), 10 clays (C; note the popped cell), or 14 days (D), STA6 cells were N starved for 4 (E) or 14 (F) days with an acetate boost. Arrows indicate starch. The magnification is the same as in FIG. 1.

Beginning at 5 days post-N-starve, obese sta6 cells become sufficiently lipid filled that they tend to float up to the meniscus of a culture tube, and they collect at the meniscus when a culture aliquot is centrifuged at 16,000×g or 100,000×g (cells normally pellet at 800×g). Full "floatability" was displayed by boosted sta6 cultures after 7 to 9 days.

Obese sta6 cultures become increasingly yellow during long-term culture, during which time their triaylakoids are all but eliminated. Although their LBs continue to increase in size, cell size itself remains fairly constant since the cells are losing both chloroplast and cytoplasmic volume. When aliquots of yellow cultures are inoculated into N-replete medium, at least some of the cells remain viable. The culture turned white when the cells died (typically after 2 weeks), at which time the cells lysed and the LBs tended to clump.

Example 8

This example illustrates long-term maintenance of N-starved STA6 cells and effects of an "acetate boost".

As documented with DEEM, the STA6 strain did not make cpst-LBs, producing LBs only in the cytoplasm. After 4 days of N starvation, these LBs appeared as brown internal spheres (white arrows in FIG. 5A) surrounded by a rim of white refractile starch, and they were visibly larger than in the 2-day sample (FIG. 1E), FIG. 5 shows STA6 cells that were N starved for 4 or more days with and without acetate boost. In (A) STA6 cells that were N starved for 4 days without acetate boost. Starch appears white at the cell periphery and darker in the interior (white arrows). Black arrow, popped cell. In (B) STA6 cells that were N starved for 4 days with an acetate boost. White arrows, interior LBs; black arrow, popped cell. In (C) STA6 cells that were N starved for 9 days with an acetate boost. In (D) STA6 cells that were N starved for 14 days with an acetate boost. The magnification is the same as in FIG. 1.

Figure 5A:
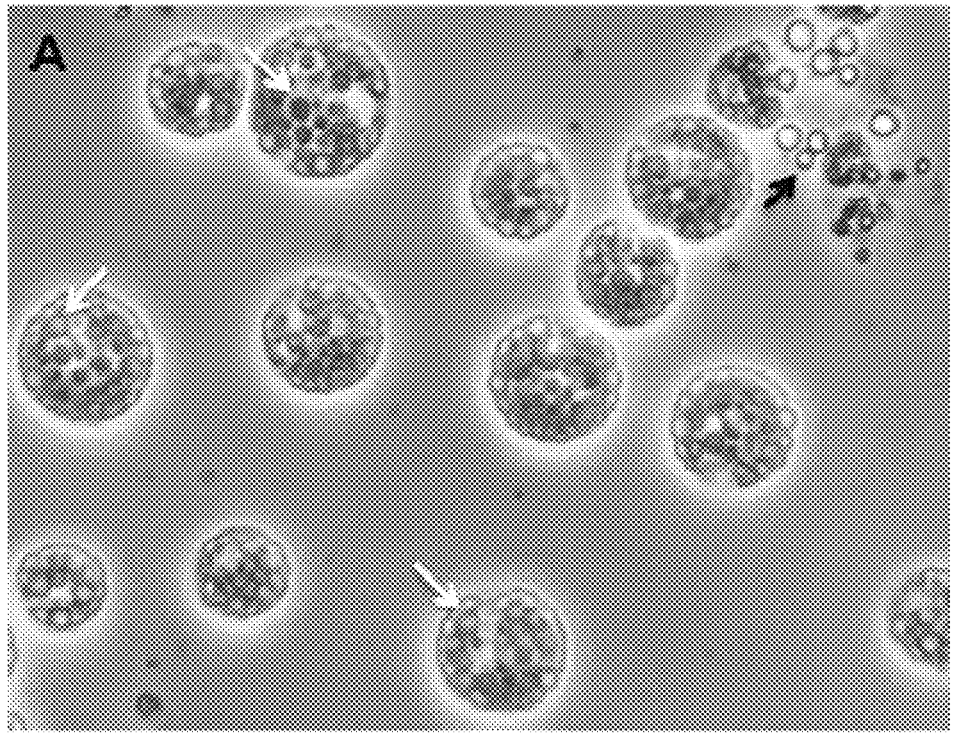
FIG. 5A illustrates STA6 cells N-starved for 4 days without acetate boost.
Figure 5B:
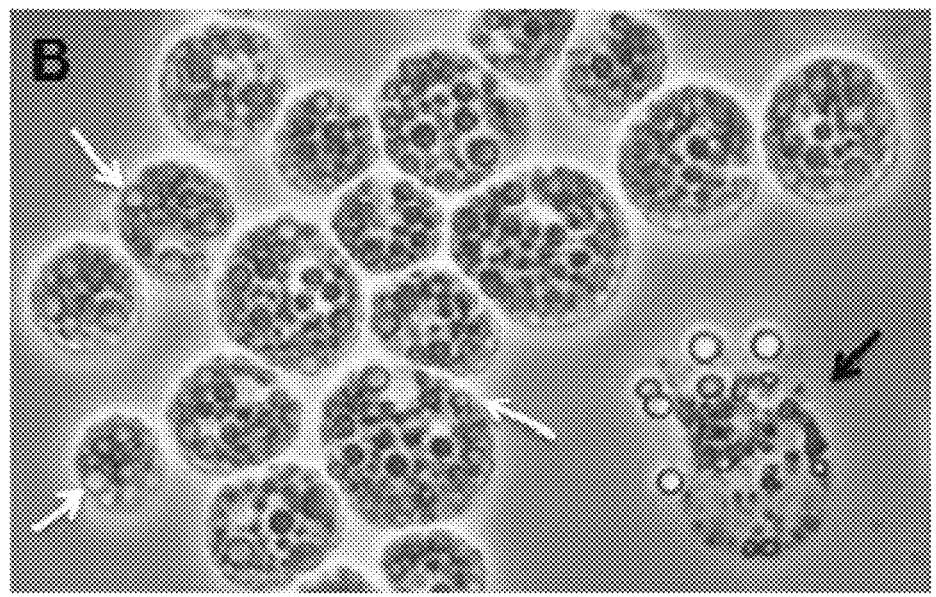
FIG. 5B illustrates STA6 cells N-starved for 4 days with an acetate boost.
Figure 5C:
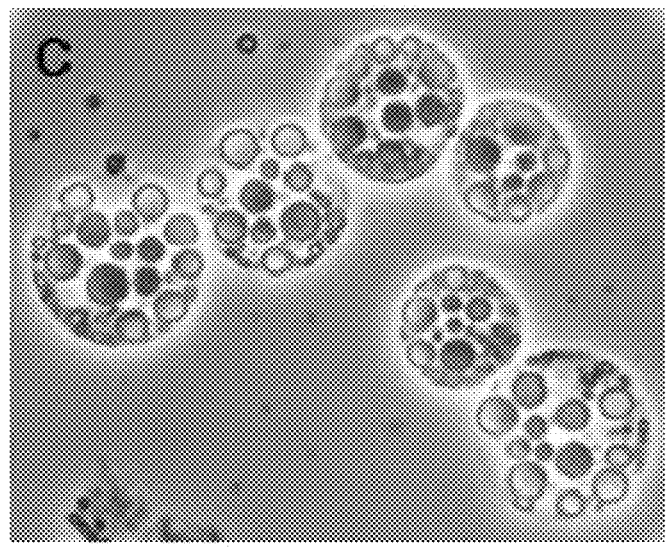
FIG. 5C illustrates STA6 cells N-starved for 9 days with an acetate boost.
Figure 5D:
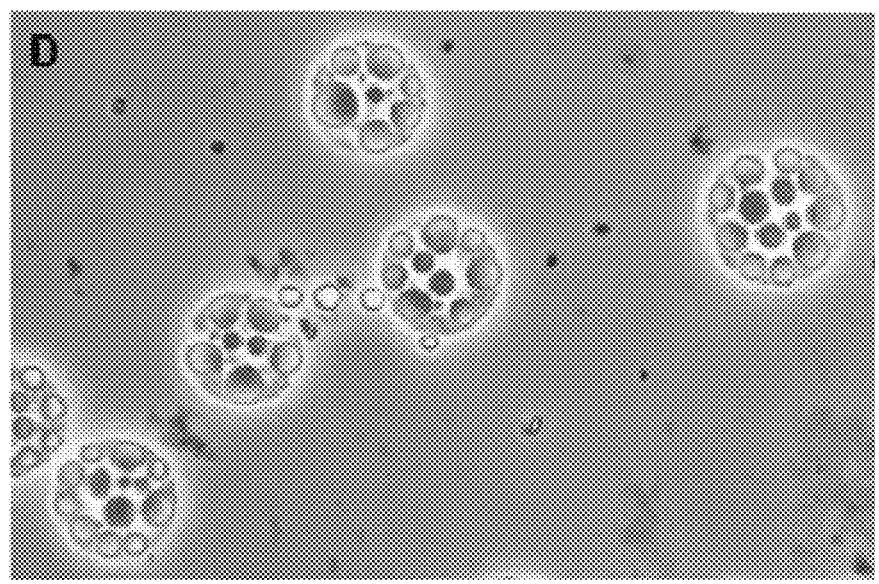
FIG. 5D illustrates STA6 cells N-starved for 14 days with an acetate boost.

When given an acetate boost after 2 days of N starvation, STA6 cells at 4 days displayed two differences from non-boosted cells (compare FIGS. 5A and B): the LBs in the boosted cells were somewhat larger, and some were located at the periphery and hence appeared lighter (white arrows in FIG. 5B). These trends continued with longer incubations: at 9 days (FIG. 5C) and 14 days (FIG. 5D), the LBs were greatly enlarged, and many had the light color imparted by a peripheral location.

Accompanying the increase in LB size and change in distribution, boosted STA6 cells deplete their starch reserves with incubation time. This is most readily seen with bright-field microscopy, where the refractile starch is easily identified. FIG. 4E and FIG. 4F contrast 4-day boosted with 14-day boosted STA6 cells, where the decrease in starch levels (white arrows) and the increase in LB size is evident. Despite this loss of starch, obese STA6 cells do not display the "floatability" of obese sta6 cells, presumably because the remaining starch is very dense (1500 kg/m3 (Sujka, M. and Jamroz, J., Int. Agrophysics. 21: 107-113, 2007)), and the majority of cells continue to pellet at 800×g out to 14 days.

Obese STA6 cultures turn yellow and die more slowly than sta6, and the cells retain more cytoplasm, possibly because the cells are provisioned with starch reserves.

Example 9

This example illustrates the number of lipid bodies per cell.

In a previous study (Wang, Z. T., et al., Eukaryot. Cell 9: 1856-68, 2009) the areas of Nile-Red-stained LBs were quantified to obtain an estimate of LB yield.

Light-microscopy images obtained in the current study are well suited to evaluation of the number of LBs per cell, regardless of size, under various induction conditions.

The STA6 strain maintained a narrow range of numbers of LBs/cell (4 to 12) during the first 96 h, while the median increased somewhat with extended culture. The sta6 strain had 1.5 to 2 times more LBs/cell than the STA6 strain at each time point, presumably due to its cpst-LB population, and the range (6 to 25 LBs/cell) was considerably larger, but the median held steady at 12 to 15 LBs/cell. While not evaluated at all time points, sta6 cells complemented with STAG transgenes showed an LB/cell distribution identical to that of the STA6 strain after 48 h N starvation, with a range of 4 to 12, a mean of 7.2, and a median of 7 (n=22).

FIG. 6 plots these findings. FIG. 6A shows number of LBs per cell, expressed as a percentage of the total cells scored in a given sample. Arrows indicate median values. STA6 cells that were N starved for 48 h, 96 h, 96 h with an acetate boost, and >96 h with an acetate boost (pooled samples up to 13 days). STA6 cells N-starved 48 hours (n=36 cells); mean=7.4±2, median=7. STA6 cells N-starved 96 hours without boost (n=43 cells): mean=9.7±1.6, median=9. STA6 cells N-starved 96 hours with acetate boost (n=65 cells); mean=8.4±1.8, median=9). STA6 cells N-starved >96 hours with boost (n=25); mean=10.1±2.3, median=10.

Figure 6B:
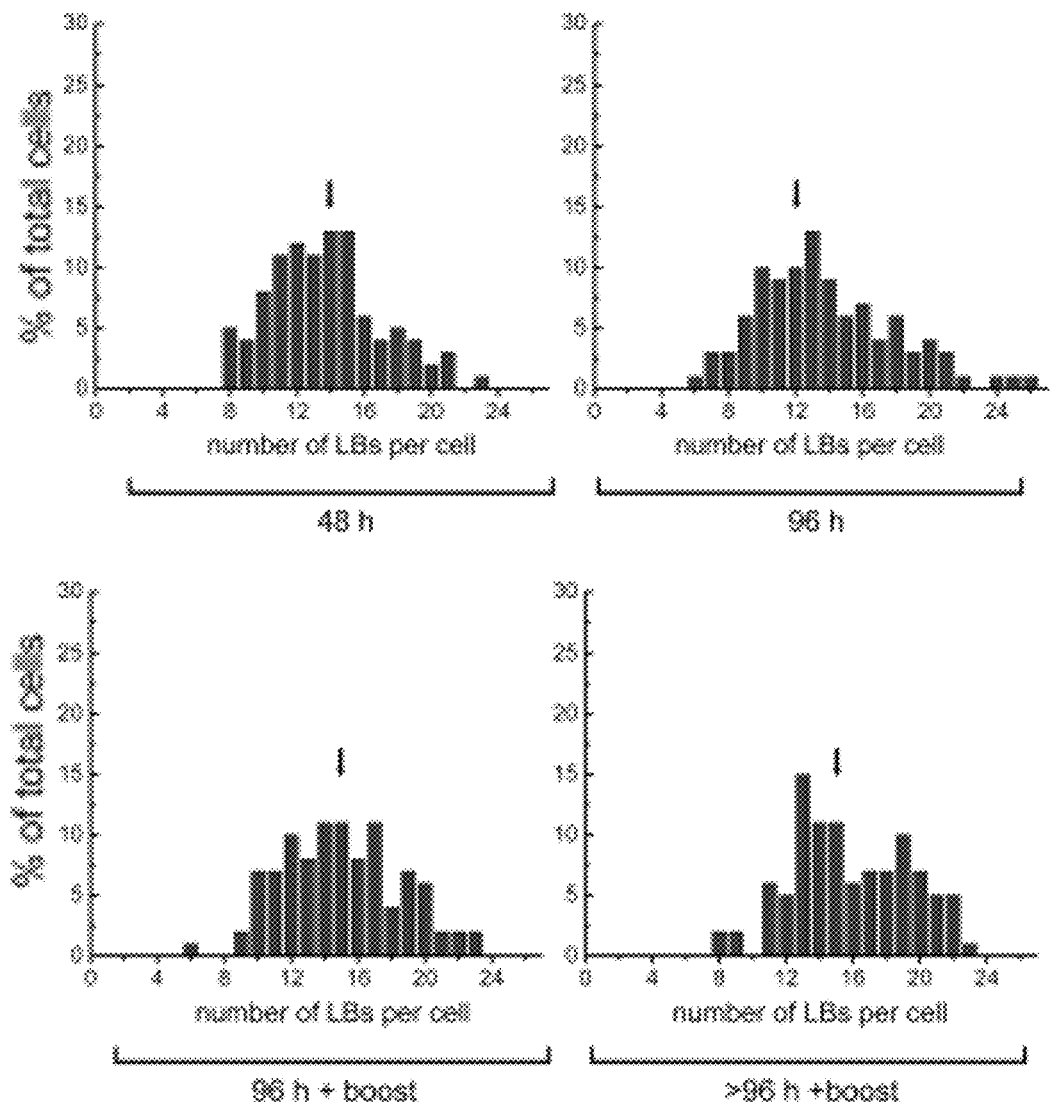
FIG. 6B illustrates sta6 cells that were N starved for 48 h, 96 h, 96 h with an acetate boost, and >96 h with an acetate boost.

FIG. 6B presents data for sta6 cells that were N starved for 48 h, 96 h, 96 h with an acetate boost, and >96 h with an acetate boost (pooled samples up to 10 days), sta6 cells N-starved 48 hours (n=110); mean=13.7±3.3, median=14. sta6 cells N-starved 96 hours without boost (n=144); mean=13.7±4.1, median=12. sta6 cells N-starved 96 hours with acetate boost (n=99); mean=15±3.5, median=15. sta6 cells N-starved >96 hours with boost (n=123); mean=15.9±3.6, median=15.

The STA6 strain maintains a narrow range of LB/cell (4-12) during the first 4 days, with the median increasing with extended culture. The sta6 strain has 1.5-2× more LB/cell than STA6 at each time point, presumably due to its cpst-LB population, and the range (6-25) is considerably larger, but the median remains constant, at 14-15, except in the non-boosted 96-hr sample where it drops to 12.

Example 10

This example illustrates neutral-lipid-containing inclusions in N-replete log-phase cells.

When N-replete C. reinhardtii cells are solvent-extracted and analyzed biochemically, low levels of TAG are detected (Li, Y., et al., Metab. Eng. 12: 387-91, 2010; Moellering, E. R. and Benning, C., Eukaryot. Cell 10: 97-106, 2010; Siaut, M., et al., BMC Biotechnology, 11: 7-22, 2011), as are low levels of Nile-Red-fluorescing bodies (Work, V. H., et al., Eukaryot. Cell 9: 1251-61, 2010), Deep-Etch Electron Microscopy (DEEM) involves pellets of live cells quick-frozen at liquid-helium, temperatures, fractured and deep-etched, and replicated, using Pt/C rotary-shadowing (Heuser, J. E., J. Elect. Microsc. 60: S3-S29, 2011). In these experiments, DEEM was used to identify 3 morphological correlates of this "constitutive TAG": eyespot granules and plastoglobules in the chloroplast and α-cyto-LBs in the cytoplasm.

Figure 7:
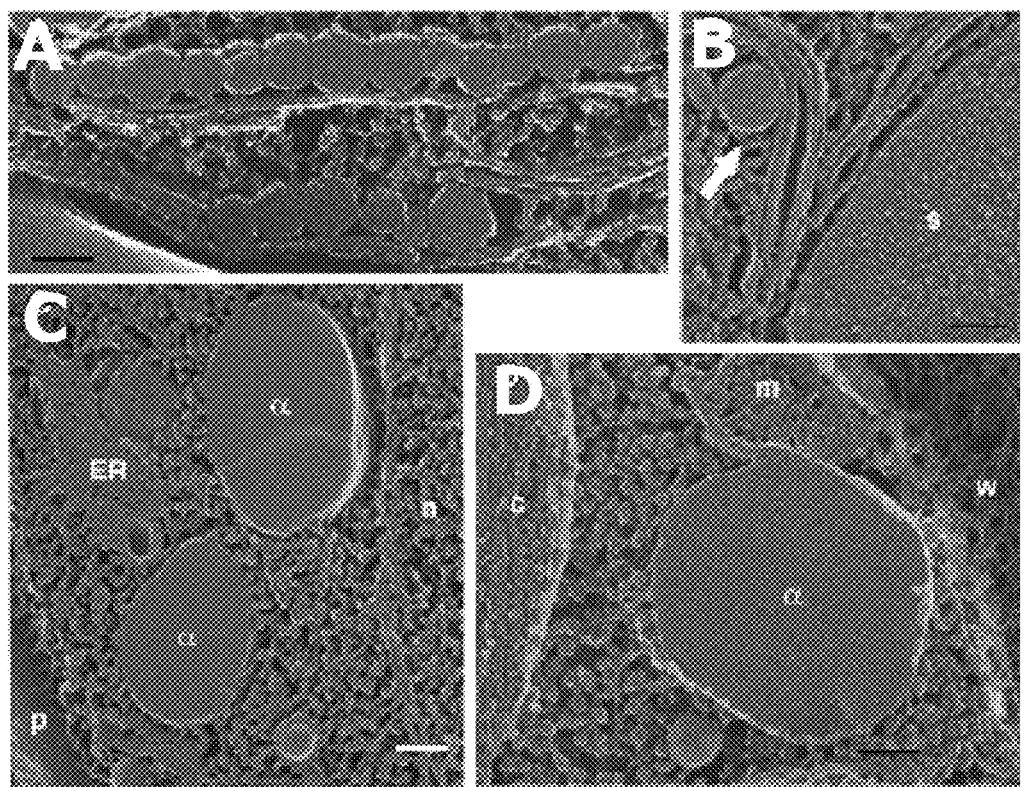
FIG. 7A illustrates eyespot granules in contact with thylakoid membranes of sta6 cell N-starved from stationary phase.
FIG. 7B illustrates plastoglobule in contact with thylakoid membrane of STA6 cell N-starved.
FIG. 7C illustrates α-cyto-LBs in contact with or proximate to ER and nuclear envelope in wild-type cell in log-phase.
FIG. 7D illustrates α-cyto-LB in contact with a mitochondrion in wild-type cell in log-phase.

In FIG. 7, (All bars 100 nm) A: Two rows of eyespot granules in contact with thylakoid membranes (sta6 30-hr N-starved from stationary phase), B: Plastoglobule (arrow) in contact with thylakoid membrane, s, starch (STA6 48-hr N-starved). C: α-cyto-LBs in contact or proximate to ER and nuclear envelope, n, nucleus; p, plasma, membrane (wt log-phase), D: α-cyto-LB in contact with a mitochondrion (m). c, chloroplast; w, cell-wall fibrils (wt log phase).

Eyespot granules (FIG. 7A), 75 to 100 nm in diameter, associate to form an opaque shield behind a circular photosensitive patch of the plasma membrane (Kreimer, G. Curr. Genet. 55: 19-43, 2009). They contain orange carotenoids (FIG. 4), and the TAG profile of purified eyespots has been characterized (Moellering, E. R. and Benning, C., Eukaryot. Cell 10: 97-106, 2010). The granules tends to be hexagonal (FIG. 7A), suggesting that the fibrillin proteins in their encapsulating membranes/coats (Schmidt, M., et al. Plant Cell. 18: 1908-30, 2006) may impose structural constraints.

Plastoglobules (FIG. 7B), 50 to 150 nm in diameter, are round proteo-membrane-limited inclusions that are ubiquitous in land-plant chloroplast (Bréhélin., C., et al., Trends Plant Sci. 12: 260-6, 2007; Kessler, F. and Vidi, P. A., Adv. Biochem. Engin. Biotechnol 107: 153-72, 2007). Presumed homologous inclusions have been reported in the stroma of certain algae (reviewed in Kreimer, G., Curr. Genet. 55: 19-43, 2009) and are first described here for C. reinhardtii. They make punctate contacts with thylakoids in the fashion of their land-plant counterparts (Austin, J. R., et al, Plant Cell. 18: 1693-1703, 2006), and their TAG endowment is inferred from their "featureless" fracture feces and from analyses of land-plant plastoglobules (Kaup, M. T., et al. Plant Physiol. 129: 1616-28, 2002). However, nothing is yet known of their protein endowment or their TAG profile, nor whether they contain pigments.

α-cyto-LBs (FIGS. 7C and 7D) presumably correspond to the bodies occasionally visualized by Nile-Red or Bodipy fluorescence in N-replete cells (Work, V. H., et al., Eukaryot Cell 9: 1251-61, 2010). They are infrequent and small, ranging in size from 250 to 1000 nm. Most are in contact, with the endoplasmic reticulum (ER) and/or nuclear envelope (FIG. 7C), and some make contact as well with mitochondria (FIG. 7D) or acidocalcisomes, but chloroplast contact, when observed, is punctate. α-cyto-LBs often localize between the chloroplast and the plasma membrane (FIG. 7D), a location never observed for the β-cyto-LBs.

Example 11

Figure 8:
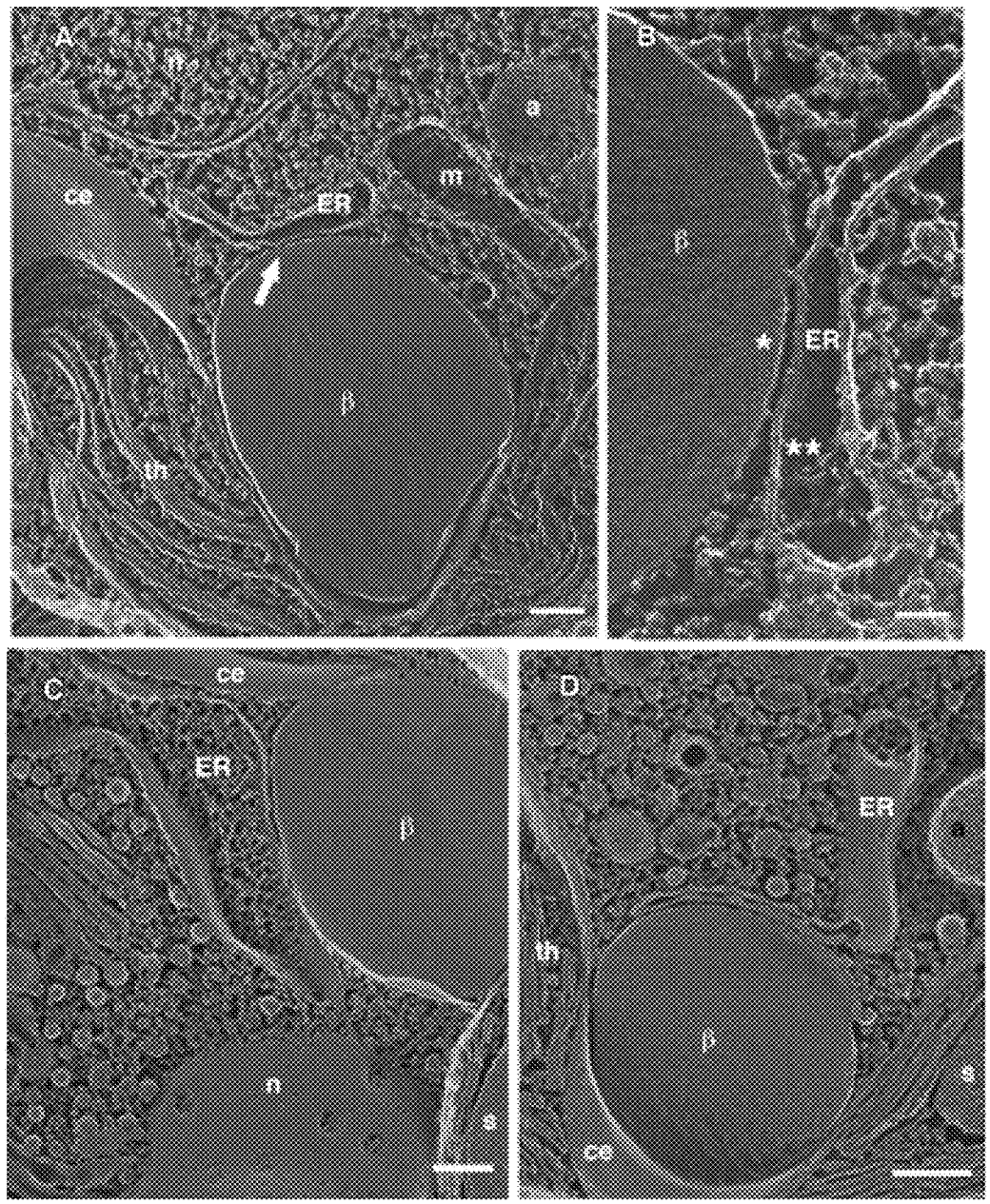
FIG. 8A illustrates a β-cyto-LB in contact with an ER element and the chloroplast.
FIG. 8B illustrates an ER membrane bilayer and LB monolayer.
FIG. 8C illustrates a β-cyto-LB in contact with an ER cisterna.
FIG. 8D illustrates β-cyto-LB in contact with a narrow ER element branching from a broader cisterna.
Figure 9:
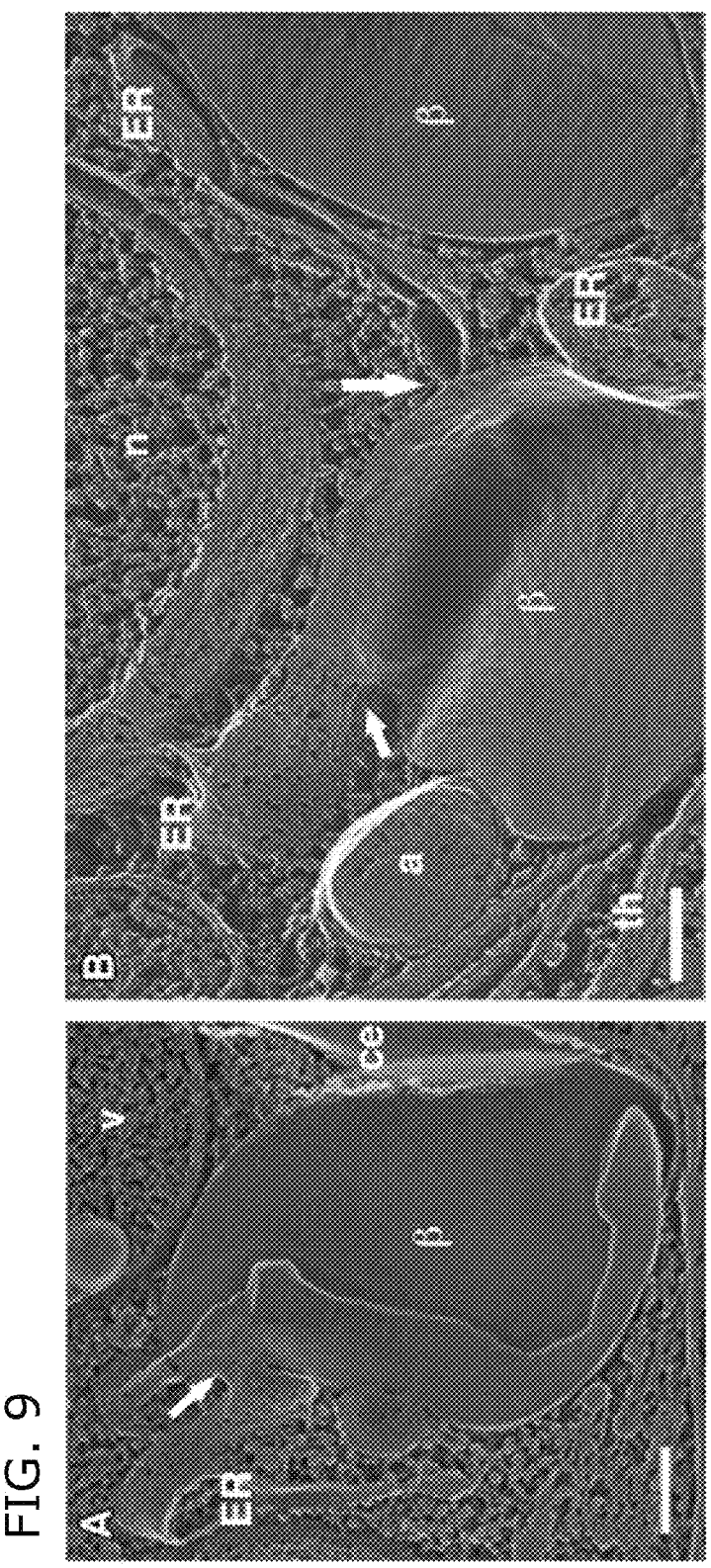
FIG. 9A illustrates a β-cyto-LB associated with an ER cisterna whose membrane flows over the LB surface.
FIG. 9B illustrates two β-cyto-LBs, the right fractured through its TAG interior, the left along its surrounding monolayer.
Figure 10:
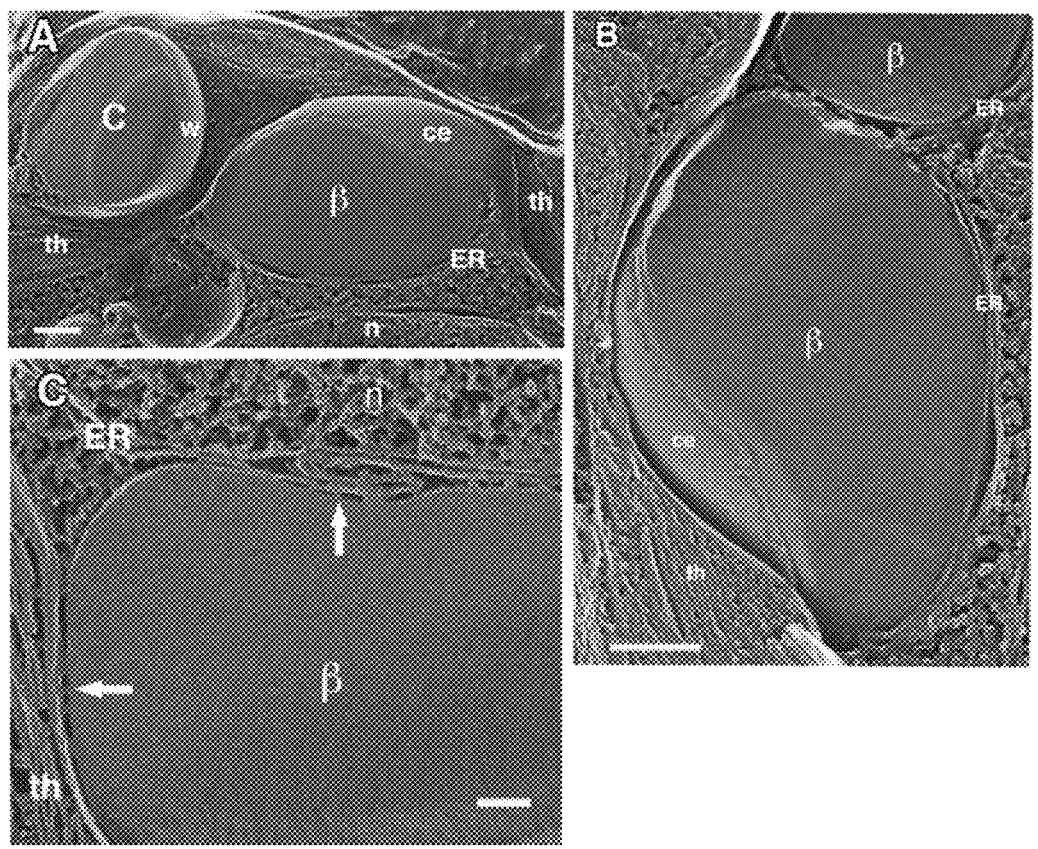
FIG. 10A illustrates a β-cyto-LB in contact, with the ER and the outer membrane of the chloroplast envelope.
FIG. 10B illustrates two contiguous β-cyto-LBs associated with the ER and the outer membrane of the chloroplast envelope.
FIG. 10C illustrates a β-cyto-LB in contact with ER/nuclear envelope.

This example illustrates the general features of β-cyto-LBs.

β-Cyto-LBs were only found in N-starved cells, first appearing ~15 hrs after transfer from log-phase growth. They became increasingly enlarged and abundant as N-starvation progressed in all strains analyzed (STA6, sta6, complemented sta6, and two wild type strains); in parallel, α-cyto-LBs became progressively uncommon and have not been encountered after 24-hr N-starvation, suggesting that they may serve to "seed" the β-cyto-LBs. In our previous study (Wang, Z. T., et al., Eukaryot. Cell 9: 1856-68, 2009), β-cyto-LBs from STA6 and sta6 cells were purified and their fatty-acid methyl esters (FAMEs) and charged polar lipids were characterized. A fraction enriched in wt β-cyto-LBs has also been analyzed (Moellering, E. R. and Benning, C., Eukaryot. Cell 10: 97-106, 2010).

β-Cyto-LBs invariably localized between the interior surface of the cup-shaped chloroplast and the nucleus (FIG. 8A), and they displayed close relationships with two membrane systems, the ER and the outer membrane of the chloroplast envelope (OMCE). Features of these relationships are shown in FIGS. 8 to 10.

FIG. 8A shows a β-cyto-LB in contact, with an ER element (arrow) and the Chloroplast. a, acidocalcisome (Ruiz et al., 2001: Docampo et al. 2010); ce, OMCE; m, mitochondrion; n, nucleus; th, thylakoids (sta6 30-hr N-starved from stationary phase) bar, 100 nm. FIG. 8B is an enlargement of 8A, showing ER membrane bilayer (double asterisks) and LB monolayer (single asterisk) bar, 50 nm. FIG. 8C: β-cyto-LB in contact with an ER cisterna that is feeding vesicles to the Golgi at middle left; contact with OMCE (ce) at top. n, nuclear envelope with, pores; s, starch granule (STA6 48-hr N-starved) bar, 250 nm. FIG. 8D: β-cyto-LB in contact with a narrow ER element branching from a broader cisterna and with the chloroplast envelope (ce). a, acidocalcisome; s, starch; th, thylakoids (STA6 48-hr N-starved) bar, 250 nm.

Example 12

This example illustrates β-Cyto-LB relationships with endoplasmic reticulum (ER).

An element of ER is almost invariably found closely associated with one surface of a β-cyto-LB, a relationship also encountered in land-plant seeds (Schmidt, M. A. and Herman, E. M., Mol. Plant, 1: 910-24, 2008) and animal cells (Fujimoto et al, 2008). Some fractures expose punctate associations as in FIG. 8A (arrow), enlarged in FIG. 8B, allowing excellent views of the continuity between the outer leaflet of the ER membrane and the lipid monolayer surrounding the β-cyto-LB, much as has been described for LB topology in other systems (Fujimoto, T. et al., Histochem. Cell Biol. 130: 263-79, 2008).

In many cases the fractures reveal extensive associations, sometimes involving up to half the β-cyto-LB surface, with numerous punctate associations between the enfolding ER and the β-cyto-LB monolayer. FIG. 8C shows a "multi-tasking" ER cisterna coming off the nuclear envelope, blebbing off vesicles to the Golgi on the left side and making extended contact with a β-cyto-LB on the right side. FIG. 8D shows a large ER cisterna giving off a narrow tubular element that makes extended β-cyto-LB contact.

FIGS. 9A and 9B show additional features of the LB/ER relationship, FIG. 9A: β-cyto-LB associated with an ER cisterna whose membrane flows over the LB surface; arrow denotes junction between intramembrane particle (IMP)-pit-rich and IMP-free domain, ce, OMCE; v, vacuole (sta6 12-hr N-starved) bar, 100 nm, FIG. 9B: Two β-cyto-LBs, the right fractured through its TAG interior, the left along its surrounding monolayer. Right arrow, ER membranes feeding directly into the IMP-free LB monolayer; left arrow, IMP-pit-rich ER, extending off the nuclear envelope, continuous with the IMP-free LB monolayer, a, acidocalcisome; n, nucleus; th, thylakoids (sta6 30-hr N-starved from stationary phase) bar, 250 nm.

In FIG. 9A, an ER membrane displays a signature array of intramembranous-particle (IMP) "pits" that form when transmembrane proteins are pulled out of the membrane during fracture. At its junction with the LB (arrow), a naked monolayer spreads over the LB surface, leaving the IMP pits behind. FIG. 9B shows two β-cyto-LBs and two ER cisternae. The cisterna to the right makes lateral contact with the one LB and then feeds directly into the second LB (rightward arrow). Such "direct feeds" have been visualized ~10 times. The cisterna to the left, coming off the nuclear envelope, makes an IMP pit/no pit junction at the leftward arrow. Such junctions complement previous findings (Wang, Z. T., et al., Eukaryot. Cell 9: 1856-68, 2009) that purified β-cyto-LBs are devoid of protein.

Example 13

This example illustrates β-Cyto-LB relationships with the outer membrane of the chloroplast envelope (OMCE).

The OMCE is almost invariably closely associated with the non-ER-associated surface of a β-cyto-LB (FIGS. 8 and 9); indeed, β-cyto LBs typically "snuggle" into infoldings of the chloroplast surface (FIGS. 8A, 8C, 8D).

FIGS. 10A to 10C show additional features of the β-cyto-LB/OMCE relationship. In FIG. 10A: β-cyto-LB with the ER in contact with one face and the OMCE (ce) flowing over the opposite face. Also shown is a chloroplast LB (C) with an IMP-free thylakoid wrap (w) flowing over its surface, n, nucleus; th, thylakoids (sta6 30-hr N-starved from stationary) bar, 250 nm. FIG. 10B: Two contiguous β-cyto-LBs associated with ER on one lace and OMCE (ce) flowing over the opposite face, th, thylakoids (sta6 30-hr N-starved from stationary) bar, 250 nm. FIG. 10C: β-Cyto-LB in contact with ER/nuclear envelope at upper arrow and with the OMCE at left arrow, n, nucleus; th, thylakoids (STA6, 48-hr N-starved) bar, 100 nm.

In FIGS. 10A and 10B, the OMCE, which is virtually IMP-free in N-starved cells (c.f. FIG. 8A), appears to "flow" over the β-cyto-LB exterior in the manner described above for the flow of ER membrane (FIGS. 9A and 9B). FIG. 10C shows these relationships in cross-fracture: a β-cyto-LB is in extensive contact with the nuclear envelope/ER on one face (upper arrow), while a second face makes a long association, with frequent punctate contacts, with the OMCE (left arrow).

Example 14

This example illustrates the relationship between α-cyto-LBs and β-cyto-LBs.

Scrutiny of hundreds of DEEM micrographs recording the early hours of N-starvation has failed to yield examples of small "nascent" β-cyto-LBs sandwiched between ER and OMCE membranes; instead, when β-cyto-LBs are first encountered at ~15 hr, they are invariably already in the size range of large α-cyto-LBs (FIG. 7D). This observation suggests that in response to N-starvation, α-cyto-LBs may "seed" the formation of β-cyto-LBs, recruiting the stable ER and OMCE associations entailed in the extensive β-cyto-LB enlargement that occurs at later stages.

Example 15

This example illustrates the general features of the cpst-LBs.

In exhaustive analyses of growing and N-starved starch-producing (STA6 and wt) cells in liquid media, on agar plates out to 30 days, and in zygotes, including 3 starch-producing sta6 strains complemented by STA6 transgenes, none has ever been observed to contain cpst-LBs.

By contrast, cpst-LBs are an invariant feature of N-starved starchless sta6 cells. In a time-course DEEM study, cpst-LBs were not detected at 2, 4, and 8 hr after sta6 cells were N-starved from log phase, but were frequently encountered at 12 hr, and they increase in size until they dominate the chloroplast stroma. In a previous study (Wang, Z. T., et al., Eukaryot. Cell 9: 1856-68, 2009), cpst-LBs were scored in popped-cell assays of sta6, but they did not contribute to purified sta6 LB preparations since the cell-breakage procedure employed was designed to leave chloroplasts intact.

Figure 11:
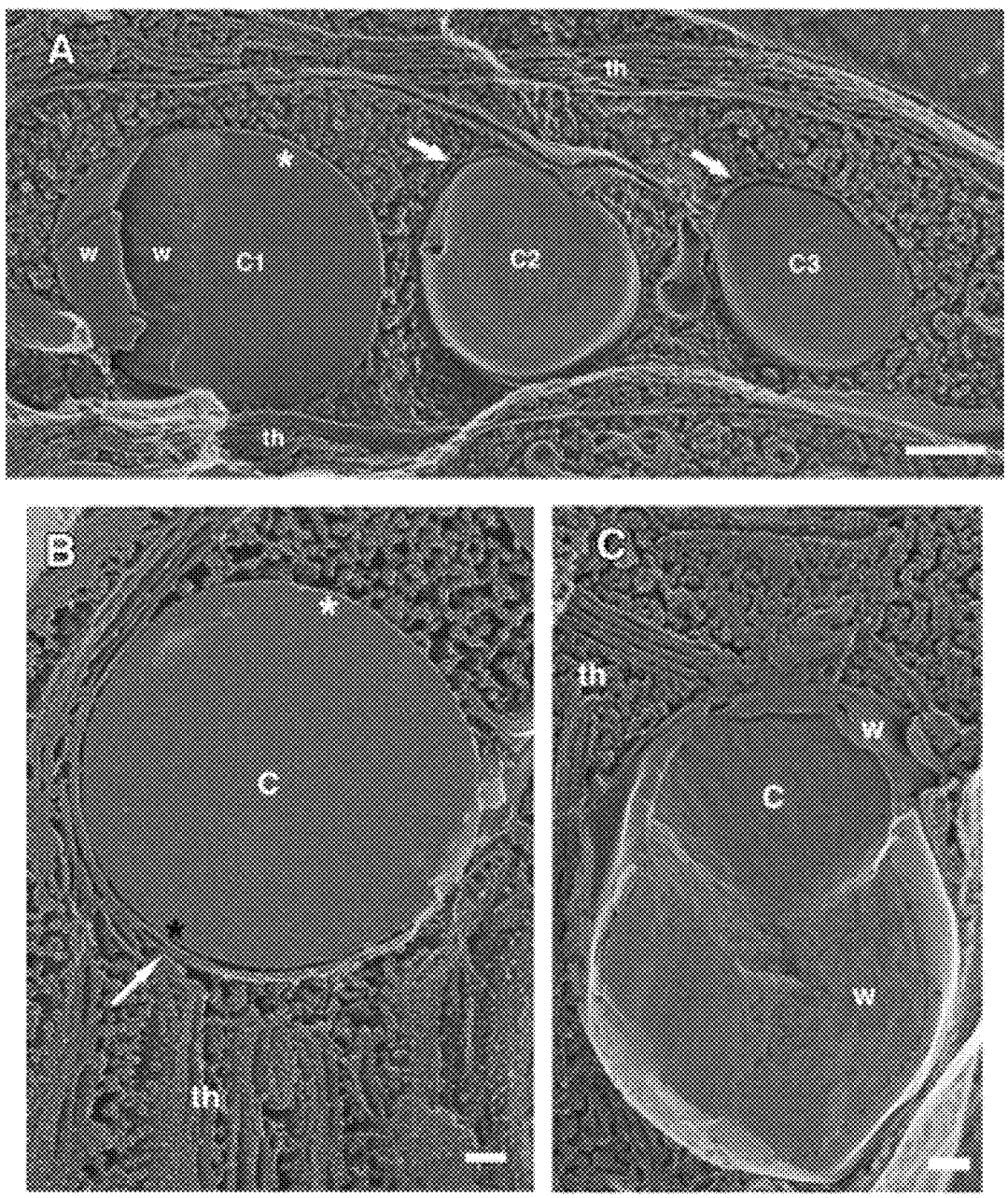
FIG. 11A illustrates three chloroplast LBs.
FIG. 11B illustrates the monolayer surface of a chloroplast LB with a thylakoid wrap.
FIG. 11C illustrates a chloroplast LB with en-face views of IMP-free thylakoid wraps.

Cpst-LBs are shown in FIGS. 10A and 11A-C. In FIG. 11A: Three cpst-LBs (C1-C3). Asterisk marks the monolayer surrounding the rightward face of C1; en-face fractured thylakoid wraps associated with C1 at w; arrows point to cross-fractured thylakoid wraps associated with C2 and C3. th, thylakoids (sta6 40-hr N-starved) bar, 250 nm. FIG. 11B: Cpst-LB (C) with white asterisk marking its monolayer surface and arrow pointing to a thylakoid wrap, where a wrap bilayer is visible at the black asterisk, thy, thylakoids replete with IMPs (sta6, 15-hr N-starved) bar, 100 nm. FIG. 11C: Cpst-LB (C) with en-face views of IMP-free thylakoid wraps (w) flowing over the LB surface, th, thylakoids (sta6 40-hr N-starved) bar, 100 nm. Degenerating thylakoids at top of field.

Each cpst-LB is delimited by a membrane monolayer; examples are indicated with asterisks in FIGS. 11A and 11B. In addition, most are at least partially enveloped by one or more thylakoids, a configuration designated the "thylakoid wrap." Cross-fractured single wraps are indicated by arrows in FIGS. 11A and 11B; en face views are labeled within FIGS. 10A and 11A and 11C, where IMP-free thylakoid membrane appears to "flow" over the cpst-LB surface, reminiscent of the ER and OMCE relationships with β-cyto-LBs as described. Images such as the upper region of FIG. 11C suggest that thylakoid membrane may also be disassembling in conjunction with cpst-LB assembly.

Example 16

This example illustrates the relationship between cpst-LBs and plastoglobules.

When first encountered in N-starved sta6 cells, cpst LBs already measure at least 0.5 μm; small, "nascent" cpst-LBs with thylakoid wraps have never been observed, albeit these might be difficult to identify. This is reminiscent of our failure, noted above, to identify nascent β-cyto-LBs. Possibly, therefore, the small plastoglobules in the chloroplast stoma serve to "seed" cpst-LB formation in sta6, with their limited thylakoid contacts shifting to the more extensive wrapped configurations, as considered more fully in the Discussion.

Example 17

This example illustrates the fine-structure of cells subjected to extended N-starvation and acetate boost.

Figure 12:
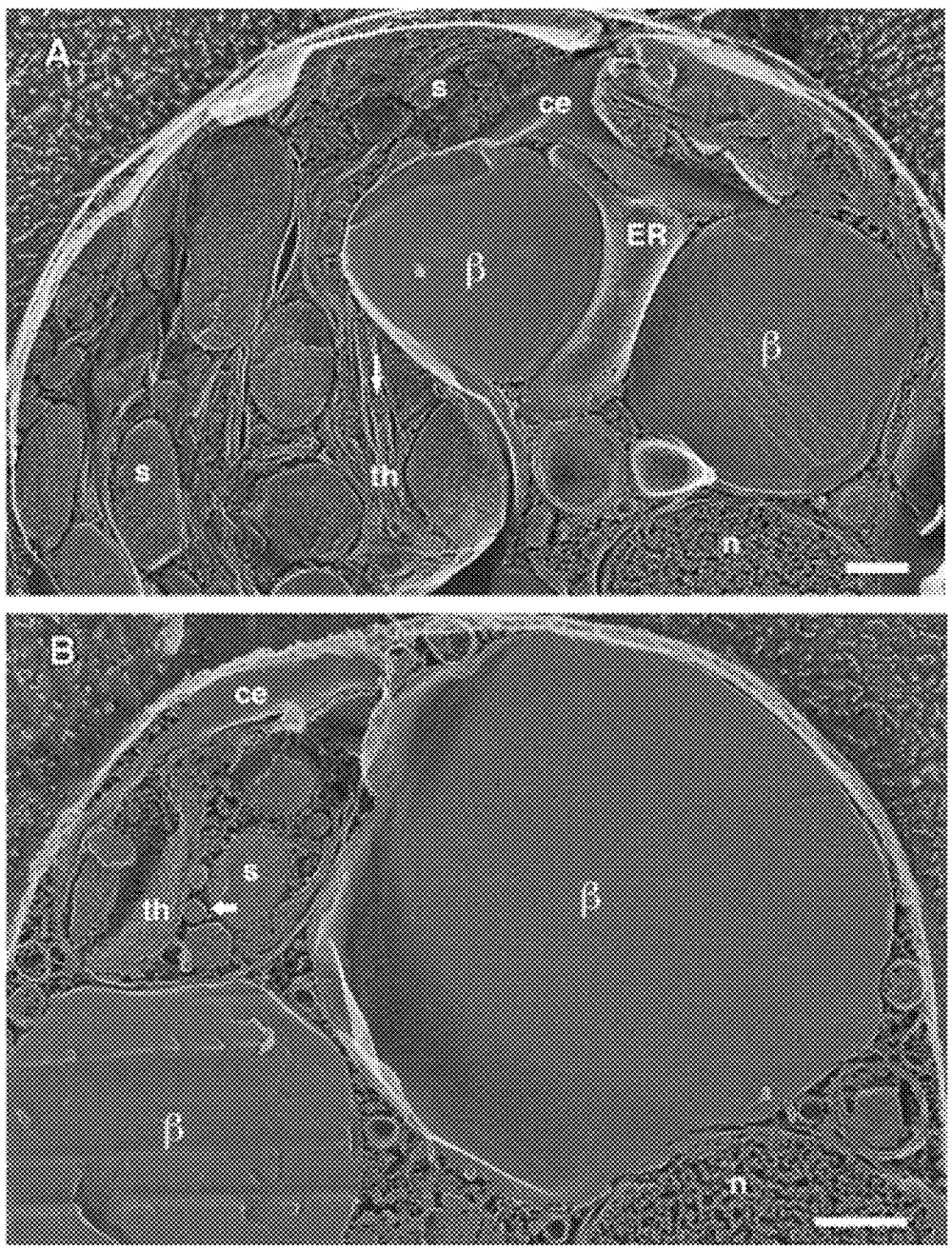
FIG. 12A illustrates STA6 cell N-starved four days with an acetate boost.
FIG. 12B illustrates STA6 cell N-starved fourteen days with an acetate boost.

FIG. 12A: STA6 cell N-starved 4 days with boost. Chloroplast is replete with starch (s) and contains extended thylakoids (th) and a plastoglobule (arrow), ce, OMCE; n, nucleus, bar, 500 nm, FIG. 12B: STA6 cell N-starved 14 days with boost. Reduced chloroplast domain contains some thylakoid stacks (th), limited starch (s), and a plastoglobule (arrow), n, nucleus; bar, 500 nm, Cannonical β-cyto-LB interactions with ER/nuclear envelope and OMCE (ce) in both A and B.

After 4 days of N starvation with an acetate boost (see above), the chloroplasts of obese STA6 cells are starch replete and contain extended thylakoids, and the β-cyto-LBs retain their canonical relationship with the ER and OMCE (FIG. 12A). After 14 days (FIG. 12B), STA6 chloroplasts are greatly reduced in size but retain, some starch, and the remaining thylakoids are extended and display IMPs. While the enormous -cyto-LBs often extend out to the cell surface, as previously noted by phase microscopy (FIG. 5), their relationship with the ER and OMCE persists.

Figure 13:
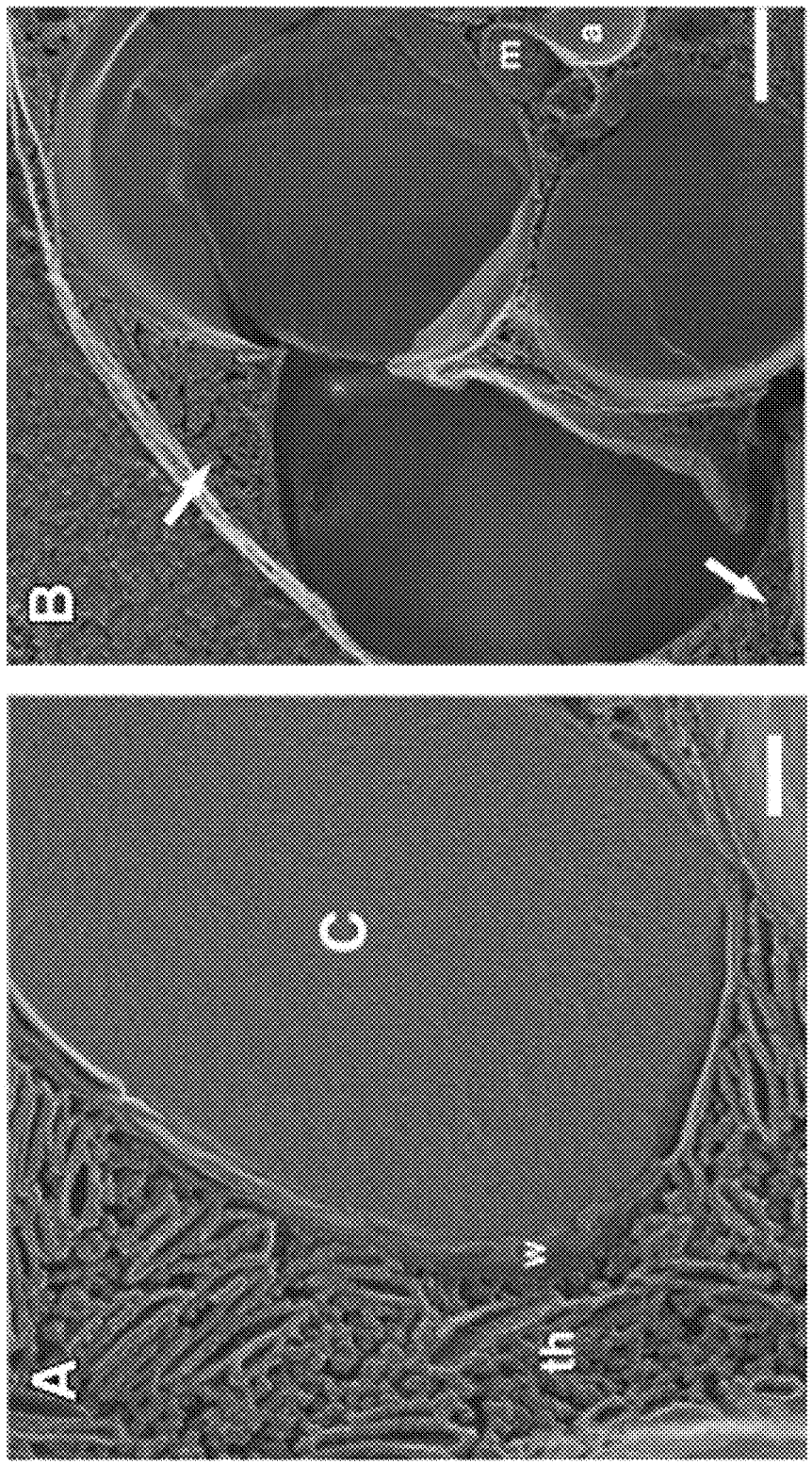
FIG. 13A illustrates sta6 cell N-starved four days with an acetate boost.
FIG. 13B illustrates sta6 cell N-starved ten days with an acetate boost.

In FIG. 13A: sta6 cell N-starved 4 days with boost. Thylakoids (th) are severed into short segments, c, cpst-LB; w, thylakoid wrap; bar, 100 nm. FIG. 13B; sta6 cell N-starved 10 days with boost. Small chloroplast regions (arrows) contain severed thylakoids. a, acidocalcisome; m, mitochondrion; bar, 500 nm.

After 4 days N-starvation with, an acetate boost, the thylakoids of sta6 cells have lost their extended configuration and are severed into short segments (FIG. 13A), a phenotype that correlates temporally with the onset of yellowing of the culture. After 10 days, the chloroplasts containing severed thylakoids are reduced to small islands (FIG. 13B), and the cellular interior is largely LBs, where it is no longer possible to distinguish cytoplasmic and chloroplast species.

Figure 14:
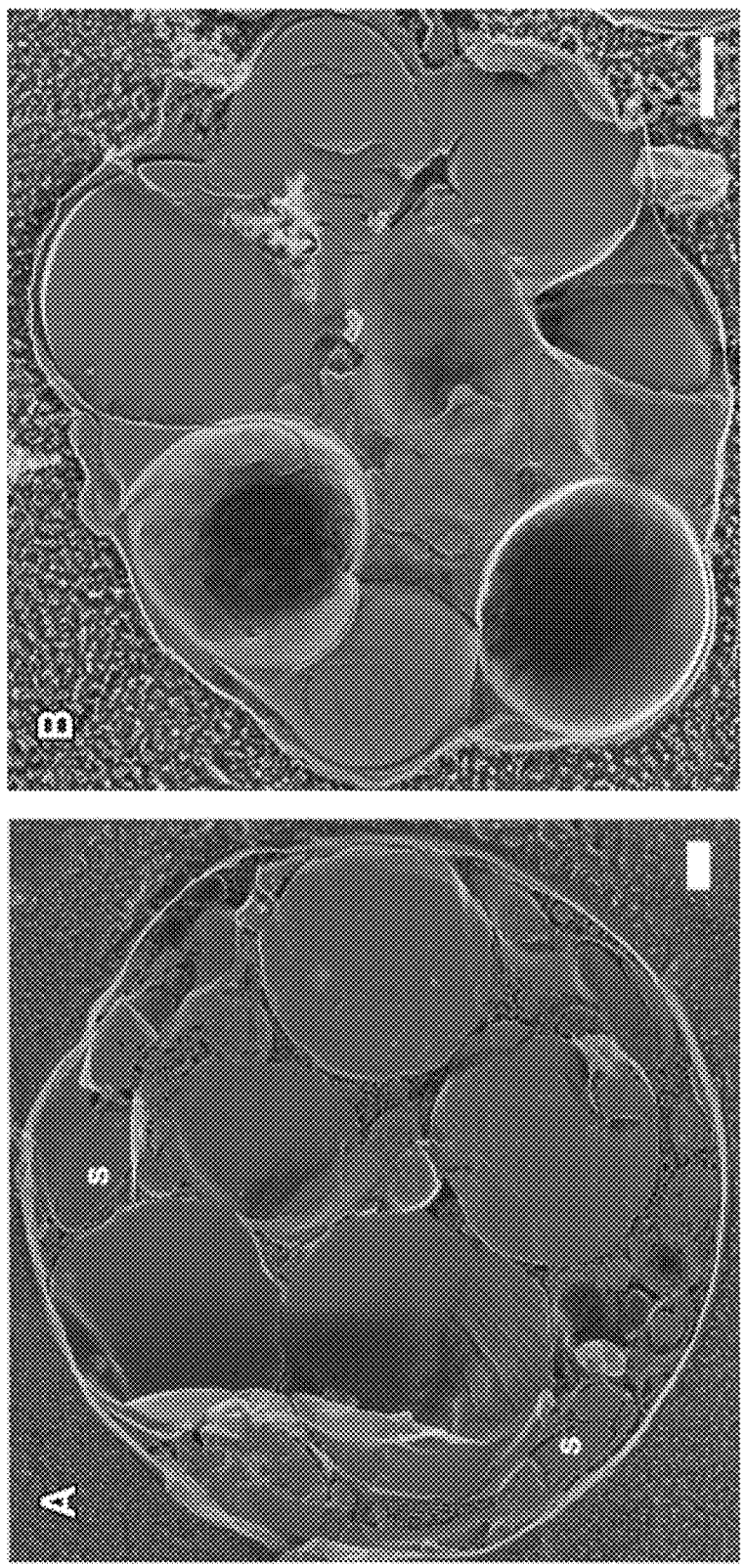
FIG. 14A illustrates a 14-day boosted obese STA6 cell.
FIG. 14B illustrates a 7-day boosted obese sta6 cell.

FIG. 14 compares a 14-day boosted obese STA 6 cell (FIG. 14A) with a 7-day boosted sta6 cell (FIG. 14B), highlighting the extreme obesity achieved by sta6 in a far shorter time period. The only identifiable organelles in such sta6 cells are the nucleus, the chloroplast envelope (which retains its normal size even when devoid of thylakoids), the eyespot (FIG. 4D), and the plasma membrane. The STA6 cells retain more cytoplasm even after an additional week of N starvation, s, starch. Bars, 500 nm.

All publications cited in this application are herein incorporated by reference in their entirety as if each individual publication, patent, patent application or other reference were specifically and individually indicated to be incorporated by reference.

What is claimed is:

1. A microorganism of strain *Chlamydomonas reinhardtii* CC4348, wherein said microorganism is buoyant in an aqueous medium.

2. A microorganism in accordance with claim 1, comprising more than 50% by dry weight triacylglycerides.

3. A microorganism in accordance with claim 1, comprising at least 60% by dry weight triacylglycerides.

4. A microorganism in accordance with claim 1, comprising at least 70% by dry weight triacylglycerides.

5. A microorganism in accordance with claim 1, wherein the microorganism is an isolated microorganism.

6. A culture of microorganisms comprising:
   a culture medium comprising an acetate; and
   a plurality of microorganisms of claim 1.

7. A culture in accordance with claim 6, wherein the culture is a culture of isolated microorganisms.

8. A culture of microorganisms comprising:
   a plurality of microorganisms of strain *Chlamydomonas reinhardtii* CC4348; and
   a culture medium, wherein the culture comprises greater than 340 mg/l triacylglycerols, wherein the plurality of microorganisms comprises microorganisms which are buoyant in an aqueous medium.

9. A culture in accordance with claim 8, wherein the culture comprises at least 360 mg/l triacylglycerols.

10. A culture in accordance with claim 8, comprising greater than 400 mg/l triacylglycerols.

11. A culture in accordance with claim 8, comprising at least 800 mg/l triacylglycerols.

12. A culture in accordance with claim 8, comprising at least 1000 mg/l triacylglycerols.

13. A culture in accordance with claim 8, comprising at least 1200 mg/l triacylglycerols.

14. A culture in accordance with claim 8, wherein the culture is a culture of isolated microorganisms.

15. A method of forming a culture comprising microorganisms of claim 1, comprising, in order:
   i) providing a population of the microorganisms growing at log phase in a first aqueous medium comprising a) at least one nitrogen source and b) at least one acetate,
   ii) replacing the first aqueous medium with a second aqueous medium, wherein the second aqueous medium comprises at least one acetate but lacks a nitrogen source;
   iii) growing the population of microorganisms in the second aqueous medium;
   iv) supplementing the second aqueous medium with additional acetate after the replacing the first aqueous medium with a second aqueous medium; and
   v) growing the population of microorganisms for at least about 3 days after supplementing the second aqueous medium with additional acetate, whereby the culture comprises greater than 340 mg/l TAG.

16. A method of forming a culture in accordance with claim 15, wherein growing the microorganisms for at least about 3 days after supplementing the second aqueous medium with additional acetate consists of growing the microorganisms for at least about 3 days up to about 12 days after supplementing the second aqueous medium with additional acetate.

17. A method of forming a culture in accordance with claim 15, wherein growing the microorganisms for at least about 3 days after supplementing the second aqueous medium with additional acetate consists of growing the microorganisms for at least 5 days up to about 7 days after supplementing the second aqueous medium with additional acetate.

18. A method of forming a culture in accordance with claim 15, wherein the growing the at least one microorganism to log phase in it liquid medium comprises growing the at least one microorganism for from about 1 day to about 3 days.

19. A method of forming a culture in accordance with claim 15, wherein the growing the at least one microorganism to log phase in a liquid medium comprises growing the at least one microorganism for about 2 days.

20. A method of forming a biofuel, comprising:
   growing a culture in accordance with claim 15; and
   harvesting cells from the culture.

21. A method of forming a biofuel in accordance with claim 20, wherein the harvesting cells comprises harvesting buoyant cells.

* * * * *